(12) United States Patent
Chang

(10) Patent No.: US 10,647,778 B2
(45) Date of Patent: May 12, 2020

(54) BI-SPECIFIC CHIMERIC ANTIGEN RECEPTOR AND USES THEREOF

(71) Applicant: University of Florida Research Foundation, Incorporated, Gainesville, FL (US)

(72) Inventor: Lung-Ji Chang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 110 days.

(21) Appl. No.: 15/549,961

(22) PCT Filed: Feb. 9, 2016

(86) PCT No.: PCT/US2016/017219
§ 371 (c)(1),
(2) Date: Aug. 9, 2017

(87) PCT Pub. No.: WO2016/130598
PCT Pub. Date: Aug. 18, 2016

(65) Prior Publication Data
US 2018/0022815 A1     Jan. 25, 2018

Related U.S. Application Data

(60) Provisional application No. 62/121,862, filed on Feb. 27, 2015, provisional application No. 62/114,045, filed on Feb. 9, 2015.

(51) Int. Cl.
| | | |
|---|---|---|
| C07K 16/28 | (2006.01) | |
| C07K 14/725 | (2006.01) | |
| A61K 39/00 | (2006.01) | |
| C07K 16/30 | (2006.01) | |
| A61K 35/12 | (2015.01) | |
| A61K 35/17 | (2015.01) | |
| C07K 14/705 | (2006.01) | |

(52) U.S. Cl.
CPC .......... *C07K 16/2896* (2013.01); *A61K 35/12* (2013.01); *A61K 35/17* (2013.01); *A61K 39/0011* (2013.01); *C07K 14/7051* (2013.01); *C07K 14/70521* (2013.01); *C07K 14/70578* (2013.01); *C07K 16/2803* (2013.01); *C07K 16/2878* (2013.01); *C07K 16/3061* (2013.01); *A61K 2039/5156* (2013.01); *A61K 2039/5158* (2013.01); *C07K 2317/31* (2013.01); *C07K 2317/622* (2013.01); *C07K 2319/02* (2013.01); *C07K 2319/03* (2013.01); *C07K 2319/33* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 9,089,520 B2 * | 7/2015 | Brenner | ............... A61K 35/17 |
| 10,117,932 B2 * | 11/2018 | Schulz | ............. A61K 39/39558 |
| 2005/0113564 A1 | 5/2005 | Campana et al. | |
| 2014/0322183 A1 | 10/2014 | Milone et al. | |
| 2015/0023937 A1 | 1/2015 | Vera Valdes et al. | |
| 2015/0118252 A1 * | 4/2015 | Ho | ................... G01N 33/56966 424/173.1 |
| 2015/0329640 A1 | 11/2015 | Finer | |
| 2016/0046724 A1 * | 2/2016 | Brogdon | ................. A61K 35/12 424/134.1 |
| 2017/0137515 A1 | 5/2017 | Chang et al. | |
| 2017/0226216 A1 * | 8/2017 | Morgan | ........... C07K 14/70578 |
| 2018/0142034 A1 | 5/2018 | Chang | |

FOREIGN PATENT DOCUMENTS

| | | |
|---|---|---|
| WO | WO 2012/033885 A1 | 3/2012 |
| WO | WO 2013/123061 A1 | 8/2013 |
| WO | WO 2013/126729 A1 | 8/2013 |
| WO | WO 2014/039523 A1 | 3/2014 |
| WO | WO 2014/055771 A1 | 4/2014 |
| WO | WO 2014/124143 A1 | 8/2014 |
| WO | WO 2014/055657 A1 | 10/2014 |
| WO | WO 2014/165707 A2 | 10/2014 |
| WO | WO 2015/142675 A2 | 9/2015 |
| WO | WO 2015/179801 A1 | 11/2015 |
| WO | WO 2016/130598 A1 | 8/2016 |

OTHER PUBLICATIONS

Prosser et al., Tumor PD-L1 co-stimulates primary human CD8+ cytotoxic T cells modified to express a PD1:CD28 chimeric receptor. Molecular Immunology 51 (2012) 263-272 (Year: 2012).*
International Search Report and Written Opinion dated May 20, 2016 for Application No. PCT/US2016/017219.
International Preliminary Report on Patentability dated Aug. 24, 2017 for Application No. PCT/US2016/017219.
International Search Report and Written Opinion dated Jun. 17, 2016 for Application No. PCT/US2016/018716.
International Preliminary Report on Patentability dated Aug. 31, 2017 for Application No. PCT/US2016/018716.
International Search Report and Written Opinion dated Sep. 14, 2015 for Application No. PCT/US2015/032245.
International Preliminary Report on Patentability dated Dec. 8, 2016 for Application No. PCT/US2015/032245.
International Search Report and Written Opinion dated Sep. 6, 2017 for Application No. PCT/US2017/030279.
Di Stasi et al., Inducible Apoptosis as a Safety Switch for Adoptive Cell Therapy. The New England Journal of Medicine. Nov. 3, 2011;365(18):1673-83.

(Continued)

Primary Examiner — Christopher M Babic
Assistant Examiner — Arthur S Leonard
(74) Attorney, Agent, or Firm — Wolf, Greenfield & Sacks, P.C.

(57) ABSTRACT

Provided herein are bi-specific chimeric antigen receptors (CARs), such as those specific for CD138 and BCMA. Use of the CARs in immune cells (e.g., T cells), compositions, and methods are also contemplated.

19 Claims, 24 Drawing Sheets

Specification includes a Sequence Listing.

(56) References Cited

OTHER PUBLICATIONS

Gargett et al., The inducible caspase-9 suicide gene system as a "safety switch" to limit on-target, off-tumor toxicities of chimeric antigen receptor T cells. Frontiers in Pharmacology. Oct. 2014;5:1-7.
Highfill et al., Anti-PD1 Therapy for Pediatric Sarcomas. Retrieved from the Internet. http://sarcomahelp.org/research/immuntherapy-pediatric-sarcomas.html#tpm2_1. May 10, 2016.
Novak et al., Expression of BCMA, TACI, and BAFF-R in multiple myeloma: a mechanism for growth and survival. Blood. Jan. 2004;103(2):689-694.
Rappl et al., The CD3-Zeta Chimeric Antigen Receptor Overcomes TCR Hypo-Responsiveness of Human Terminal Late-Stage T Cells. PLoS One. 2012;7(1):e30713:1-10.
Sadelain et al., The Basic Principles of Chimeric Antigen Receptor Design. Cancer Discovery. Apr. 2013;3(4):388-98.
Wu et al., The IL-15 receptor α chain cytoplasmic domain is critical for normal IL-15R α function but is not required for trans-presentation. Blood. Sep. 2008;112(12):4411-4419.
U.S. Appl. No. 15/552,071, filed Aug. 18, 2017, Chang.
U.S. Appl. No. 15/312,370, filed Nov. 18, 2016, Chang et al.
PCT/US2016/017219, May 20, 2016, International Search Report and Written Opinion.
PCT/US2016/017219, Aug. 24, 2017, International Preliminary Report on Patentability.
PCT/US2016/018716, Jun. 17, 2016, International Search Report and Written Opinion.
PCT/US2016/018716, Aug. 31, 2017, International Preliminary Report on Patentability.
PCT/US2015/032245, Sep. 14, 2015, International Search Report and Written Opinion.
PCT/US2015/032245, Dec. 8, 2016, International Preliminary Report on Patentability.
PCT/US2017/030279, Sep. 6, 2017, International Search Report and Written Opinion.
Supplementary European Search Report dated Jun. 12, 2018 for Application No. EP 16749750.2.
Partial Supplementary European Search Report dated Jul. 27, 2018 for Application No. EP 16753166.4.
Callahan et al., At the bedside: CTLA-4- and PD-1-blocking antibodies in cancer immunotherapy. J Leukoc Biol. Jul. 2013;94(1):41-53. doi: 10.1189/jlb.1212631. Epub May 10, 2013.
Genbank Submission; "AAT18_RS09785 hypothetical protein [Rhodococcus aetherivorans]", Gene ID: 29568086, updated on Apr. 20, 2017. 2 pages.
Genbank Submission; NIH/NCBI, Accession No. NP_001183.2: "TNFRSF17 TNF receptor superfamily member 17[*Homo sapiens*]", Gene ID: 608. Last updated on Sep. 30, 2018. 5 pages.
Genbank Submission; NIH/NCBI, Accession No. NP_002988.2: "syndecan-1 precursor [*Homo sapiens*]", Nov. 5, 2002. 2 pages.
Heczey et al., Invariant NKT cells with chimeric antigen receptor provide a novel platform for safe and effective cancer immunotherapy. Blood. Oct. 30, 2014;124(18):2824-33. doi: 10.1182/blood-2013-11-541235. Epub Jul. 21, 2014.
Lee et al., The future is now: chimeric antigen receptors as new targeted therapies for childhood cancer. Clin Cancer Res. May 15, 2012;18(10):2780-90. doi: 10.1158/1078-0432.CCR-11-1920.
Sherbenou et al., The development of potential antibody-based therapies for myeloma. Blood Rev. Mar. 2015;29(2):81-91. doi: 10.1016/j.blre.2014.09.011. Epub Sep. 28, 2014.
Song et al., CD27 costimulation augments the survival and antitumor activity of redirected human T cells in vivo. Blood. Jan. 19, 2012;119(3):696-706. doi: 10.1182/blood-2011-03-344275. Epub Nov. 23, 2011.
U.S. Appl. No. 16/097,437, filed Oct. 29, 2018, Rivkees et al.
EP 16749750.2, Jun. 12, 2018, Supplementary European Search Report.
EP 16753166.4, Jul. 27, 2018, Partial Supplementary European Search Report.
EP 16753166.4, Nov. 6, 2018, Supplementary European Search Report.
PCT/US2017/030279, Nov. 8, 2018, International Preliminary Report on Patentability.
International Preliminary Report on Patentability dated Nov. 8, 2018 for Application No. PCT/US2017/030279.
Supplementary European Search Report dated Nov. 6, 2018 for Application No. EP 16753166.4.

* cited by examiner

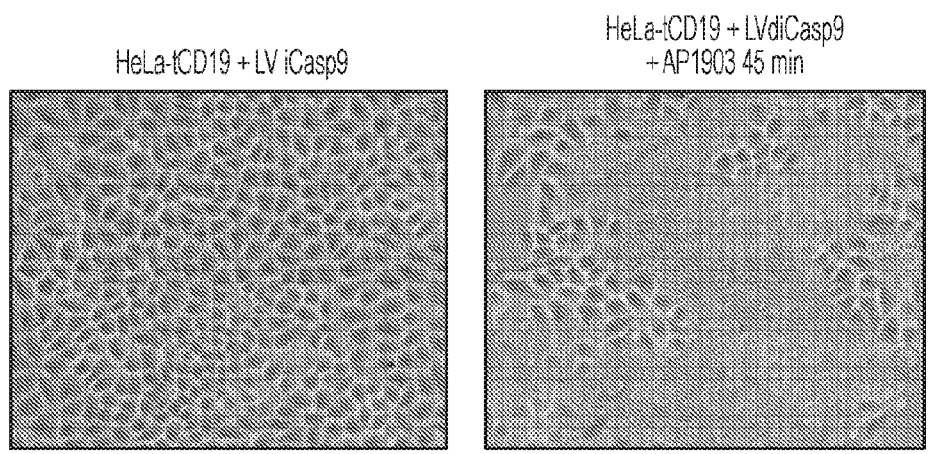
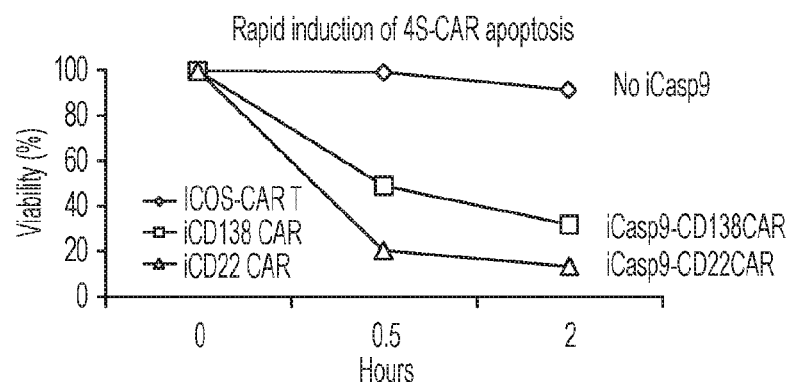
FIG. 2B

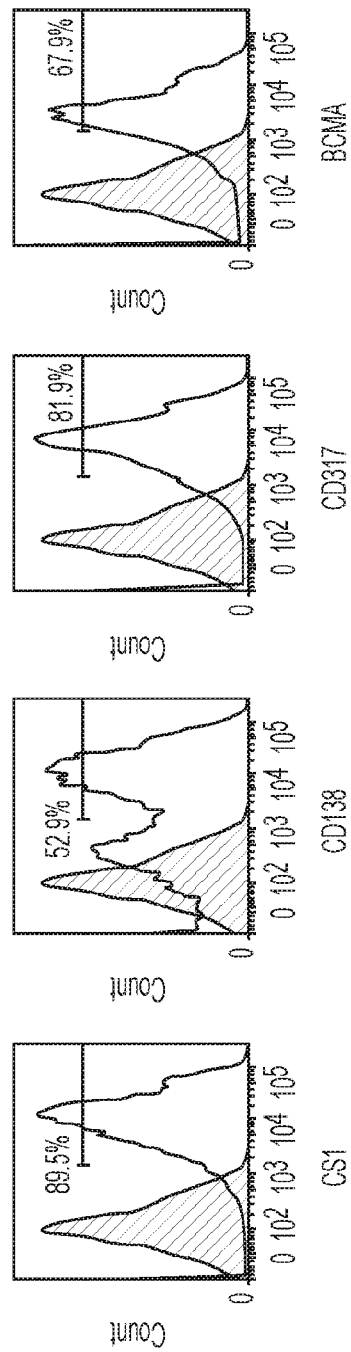

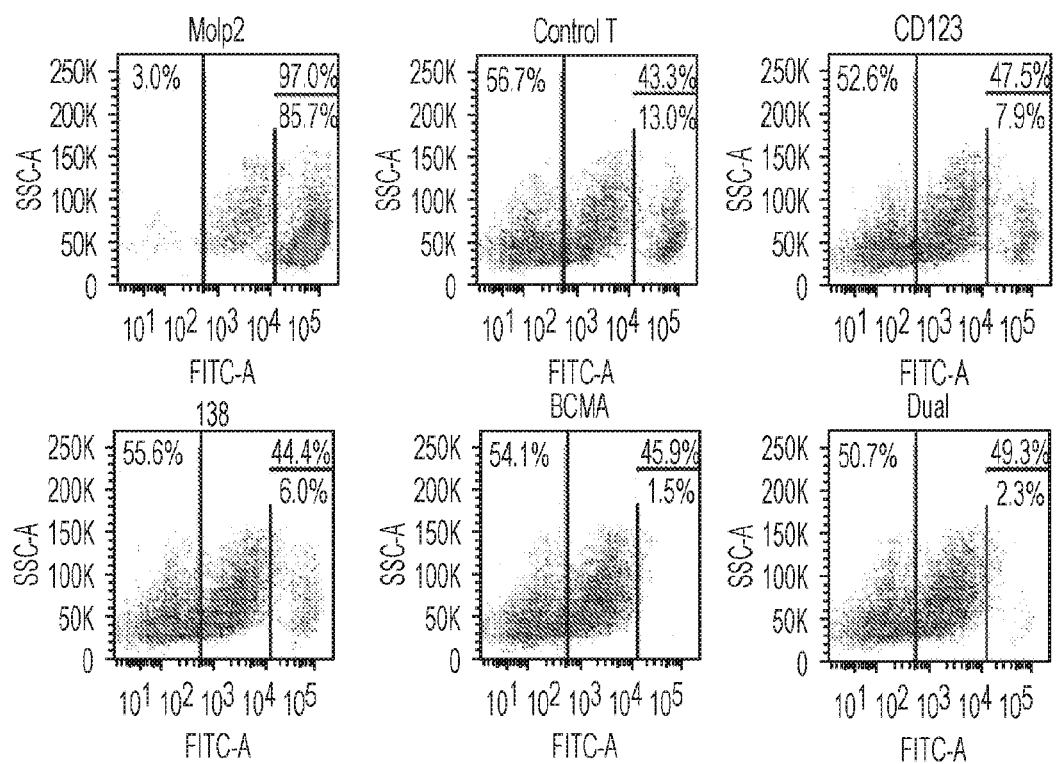
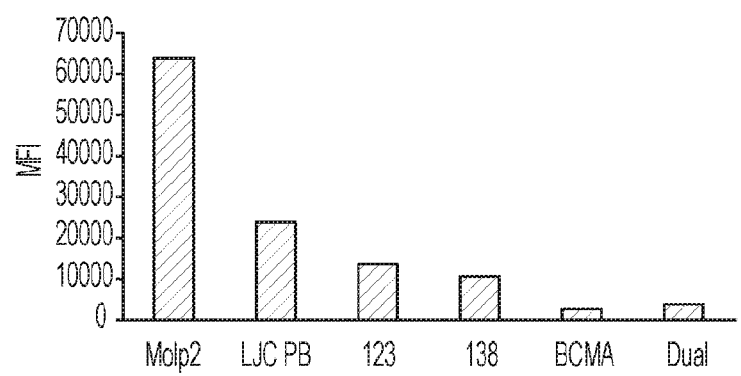
FIG. 10A

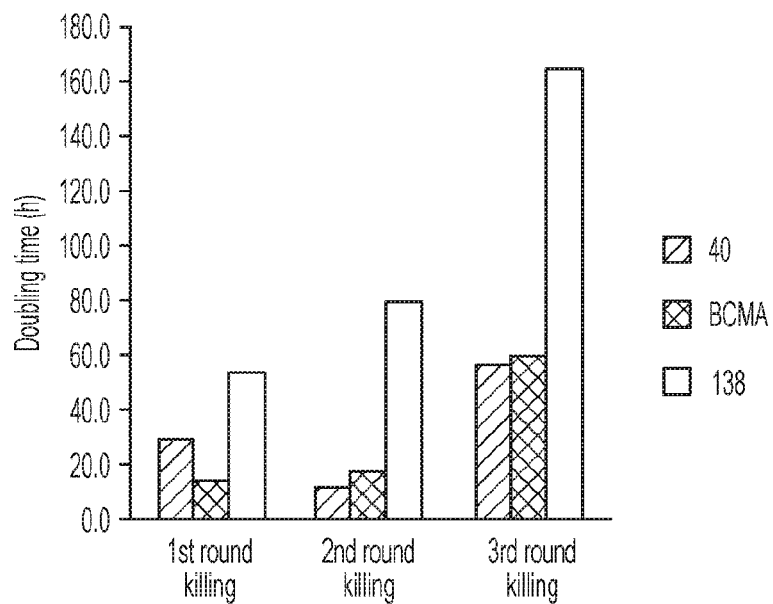
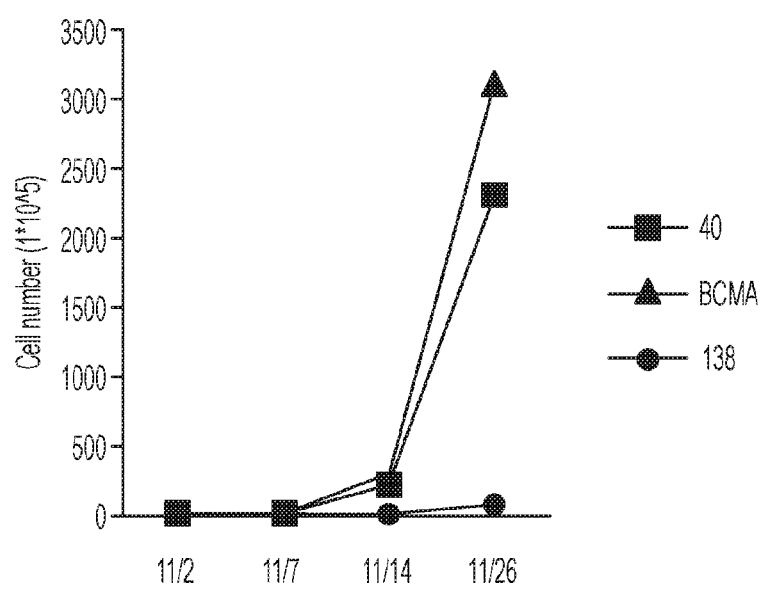
FIG. 10D

SEQUENCE LISTING

```
<160> NUMBER OF SEQ ID NOS: 38

<210> SEQ ID NO 1
<211> LENGTH: 310
<212> TYPE: PRT
<213> ORGANISM: Homo sapiens

<400> SEQUENCE: 1

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
```

```
                35                  40                  45
Ala Gly Ala Leu Gln Asp Ile Thr Leu Ser Gln Gln Thr Pro Ser Thr
 50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
                100                 105                 110

Gly Leu Thr Ala Arg Glu Gln Glu Ala Thr Pro Arg Pro Arg Glu Thr
                115                 120                 125

Thr Gln Leu Pro Thr Thr His Gln Ala Ser Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
                180                 185                 190

Glu Asp Gly Ala Ser Ser Gln Leu Pro Ala Ala Glu Gly Ser Gly Glu
                195                 200                 205

Gln Asp Phe Thr Phe Glu Thr Ser Gly Glu Asn Thr Ala Val Val Ala
                210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
                260                 265                 270

Phe Met Leu Tyr Arg Met Lys Lys Lys Asp Glu Gly Ser Tyr Ser Leu
                275                 280                 285

Glu Glu Pro Lys Gln Ala Asn Gly Gly Ala Tyr Gln Lys Pro Thr Lys
                290                 295                 300

Gln Glu Glu Phe Tyr Ala
305                 310

<210> SEQ ID NO 2
<211> LENGTH: 293
<212> TYPE: PRT
<213> ORGANISM: Homo sapiens

<400> SEQUENCE: 2

Gln Pro Ala Leu Pro Gln Ile Val Ala Thr Asn Leu Pro Pro Glu Asp
 1               5                  10                  15

Gln Asp Gly Ser Gly Asp Asp Ser Asp Asn Phe Ser Gly Ser Gly Ala
                 20                  25                  30

Gly Ala Leu Gln Asp Ile Thr Leu Ser Gln Gln Thr Pro Ser Thr Trp
                 35                  40                  45

Lys Asp Thr Gln Leu Leu Thr Ala Ile Pro Thr Ser Pro Glu Pro Thr
 50                  55                  60

Gly Leu Glu Ala Thr Ala Ala Ser Thr Ser Thr Leu Pro Ala Gly Glu
 65                  70                  75                  80

Gly Pro Lys Glu Gly Glu Ala Val Val Leu Pro Glu Val Glu Pro Gly
                 85                  90                  95
```

```
Leu Thr Ala Arg Glu Gln Glu Ala Thr Pro Arg Pro Arg Glu Thr Thr
            100                 105                 110

Gln Leu Pro Thr Thr His Gln Ala Ser Thr Thr Ala Thr Thr Ala
        115                 120                 125

Gln Glu Pro Ala Thr Ser His Pro His Arg Asp Met Gln Pro Gly His
    130                 135                 140

His Glu Thr Ser Thr Pro Ala Gly Pro Ser Gln Ala Asp Leu His Thr
145                 150                 155                 160

Pro His Thr Glu Asp Gly Gly Pro Ser Thr Glu Arg Ala Ala Glu
                165                 170                 175

Asp Gly Ala Ser Ser Gln Leu Pro Ala Ala Glu Gly Ser Gly Glu Gln
            180                 185                 190

Asp Phe Thr Phe Glu Thr Ser Gly Glu Asn Thr Ala Val Val Ala Val
            195                 200                 205

Glu Pro Asp Arg Arg Asn Gln Ser Pro Val Asp Gln Gly Ala Thr Gly
            210                 215                 220

Ala Ser Gln Gly Leu Leu Asp Arg Lys Glu Val Leu Gly Gly Val Ile
225                 230                 235                 240

Ala Gly Gly Leu Val Gly Leu Ile Phe Ala Val Cys Leu Val Gly Phe
                245                 250                 255

Met Leu Tyr Arg Met Lys Lys Lys Asp Glu Gly Ser Tyr Ser Leu Glu
                260                 265                 270

Glu Pro Lys Gln Ala Asn Gly Gly Ala Tyr Gln Lys Pro Thr Lys Gln
            275                 280                 285

Glu Glu Phe Tyr Ala
        290

<210> SEQ ID NO 3
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 3

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160
```

-continued

Thr Asn Asp Tyr Cys Lys Ser Leu Pro Ala Ala Leu Ser Ala Thr Glu
            165                 170                 175

Ile Glu Lys Ser Ile Ser Ala Arg
            180

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

Gly Gly Gly Ser
1

<210> SEQ ID NO 5
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 5

Gly Gly Gly Gly Ser
1               5

<210> SEQ ID NO 6
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 6

Gly Ser Thr Ser Gly Gly Gly Ser Gly Gly Gly Ser Gly Gly Gly Gly
1               5                   10                  15

Ser Ser

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Gly Gly Gly Gly Ser Gly Gly Gly
1               5

<210> SEQ ID NO 8
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 8

Gly Ser Thr Ser Gly Ser Gly Lys Pro Gly Ser Ser Glu Gly Ser Thr
1               5                   10                  15

Lys Gly

<210> SEQ ID NO 9
<211> LENGTH: 10
<212> TYPE: PRT

```
<213> ORGANISM: Artificial Sequence
<220> FEATURE:
<223> OTHER INFORMATION: Synthetic polypeptide

<400> SEQUENCE: 9

Gly Gly Gly Gly Ser Gly Gly Gly Gly Ser
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

Val Glu Pro Lys Ser Cys Asp Lys Thr His Thr Cys Pro Pro Cys Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 12

Leu Asp Pro Lys Ser Ser Asp Lys Thr His Thr Cys Pro Pro Cys Pro
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Val Glu Pro Lys Ser Pro Asp Lys Thr His Thr Cys Pro Pro Cys Pro
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 14

Leu Asp Lys Thr His Thr Cys Pro Pro Cys Pro
1               5                   10

<210> SEQ ID NO 15
<211> LENGTH: 122
<212> TYPE: PRT
<213> ORGANISM: Artificial Sequence
```

<220> FEATURE:
<223> OTHER INFORMATION: Synthetic polypeptide

<400> SEQUENCE: 15

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 16

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys
            100                 105

<210> SEQ ID NO 17
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Gln Trp Val Arg Gln Ala Pro Gly Gln Gly Leu Glu Trp Met
        35                  40                  45

Gly Trp Ile Gln Thr Glu Thr Arg Glu Pro Ala Tyr Ala Tyr Asp Phe
        50                  55                  60
Arg Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Leu Asp Tyr Ser Tyr Ala Met Asp Tyr Trp Gly Gln Gly Thr Leu
            100                 105                 110
Val Thr Val Ser Ser
        115

<210> SEQ ID NO 18
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 18

Asp Ile Val Leu Thr Gln Ser Pro Ala Ser Leu Ala Val Ser Leu Gly
1               5                   10                  15
Asp Arg Ala Thr Ile Asn Cys Arg Ala Ser Glu Ser Val Ser Val Ile
            20                  25                  30
Gly Ala His Leu Ile His Trp Tyr Gln Gln Lys Pro Gly Gln Pro Pro
        35                  40                  45
Lys Leu Leu Ile Tyr Leu Ala Ser Asn Leu Glu Thr Gly Val Pro Ala
    50                  55                  60
Arg Phe Ser Gly Ser Gly Ser Gly Thr Asp Phe Thr Leu Thr Ile Ser
65                  70                  75                  80
Ser Leu Gln Ala Glu Asp Ala Ala Ile Tyr Tyr Cys Leu Gln Ser Arg
                85                  90                  95
Ile Phe Pro Arg Thr Phe Gly Gln Gly Thr Lys Leu Glu Ile Lys
            100                 105                 110

<210> SEQ ID NO 19
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 19

Tyr Val Asn Gln Thr Asp Ile Tyr Phe Cys Lys Ile Glu Val Met Tyr
1               5                   10                  15
Pro Pro Pro Tyr Leu Asp Asn Glu Lys Ser Asn Gly Thr Ile Ile His
            20                  25                  30
Val Lys Gly Lys His Leu Cys Pro Ser Pro Leu Phe Pro Gly Pro Ser
        35                  40                  45
Lys Pro
    50

<210> SEQ ID NO 20
<211> LENGTH: 202
<212> TYPE: PRT
<213> ORGANISM: Artificial Sequence
<220> FEATURE:
<223> OTHER INFORMATION: Synthetic polypeptide

<400> SEQUENCE: 20

Asn Lys Ile Leu Val Lys Gln Ser Pro Met Leu Val Ala Tyr Asp Asn

```
            1               5                   10                  15
          Ala Val Asn Leu Ser Cys Lys Tyr Ser Tyr Asn Leu Phe Ser Arg Glu
                          20                  25                  30

Phe Arg Ala Ser Leu His Lys Gly Leu Asp Ser Ala Val Glu Val Cys
                          35                  40                  45

Val Val Tyr Gly Asn Tyr Ser Gln Gln Leu Gln Val Tyr Ser Lys Thr
               50                  55                  60

Gly Phe Asn Cys Asp Gly Lys Leu Gly Asn Glu Ser Val Thr Phe Tyr
          65                  70                  75                  80

Leu Gln Asn Leu Tyr Val Asn Gln Thr Asp Ile Tyr Phe Cys Lys Ile
                              85                  90                  95

Glu Val Met Tyr Pro Pro Tyr Leu Asp Asn Glu Lys Ser Asn Gly
                          100                 105                 110

Thr Ile Ile His Val Lys Gly Lys His Leu Cys Pro Ser Pro Leu Phe
                          115                 120                 125

Pro Gly Pro Ser Lys Pro Phe Trp Val Leu Val Val Gly Gly Val
                          130                 135                 140

Leu Ala Cys Tyr Ser Leu Leu Val Thr Val Ala Phe Ile Ile Phe Trp
          145                 150                 155                 160

Val Arg Ser Lys Arg Ser Arg Leu Leu His Ser Asp Tyr Met Asn Met
                              165                 170                 175

Thr Pro Arg Arg Pro Gly Pro Thr Arg Lys His Tyr Gln Pro Tyr Ala
                          180                 185                 190

Pro Pro Arg Asp Phe Ala Ala Tyr Arg Ser
                          195                 200

<210> SEQ ID NO 21
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 21

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 22
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 22

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
                35                  40                  45

Val Leu Ala Cys Tyr Ser Leu Leu Val Thr Val Ala Phe Ile Ile Phe
            50                  55                  60

Trp Val Arg Ser Lys Arg Ser Arg Leu Leu His Ser Asp Tyr Met Asn
65                  70                  75                  80
```

Met Thr Pro Arg Arg Pro Gly Pro Thr Arg Lys His Tyr Gln Pro Tyr
            85                  90                  95

Ala Pro Pro Arg Asp Phe Ala Ala Tyr Arg Ser Ala Ser
            100                 105

<210> SEQ ID NO 23
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 23

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 24
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 24

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 25

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg 65                  70                  75                  80
Arg Arg Gly Lys Gly His Asp Gly Leu Tyr Gln Gly Leu Ser Thr Ala
                    85                  90                  95
Thr Lys Asp Thr Tyr Asp Ala Leu His Met Gln Ala Leu Pro Pro Arg
            100                 105                 110

<210> SEQ ID NO 26
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 26

Arg Ser Lys Arg Ser Arg Leu Leu His Ser Asp Tyr Met Asn Met Thr
1               5                   10                  15
Pro Arg Arg Pro Gly Pro Thr Arg Lys His Tyr Gln Pro Tyr Ala Pro
                20                  25                  30
Pro Arg Asp Phe Ala Ala Tyr Arg Ser
            35                  40

<210> SEQ ID NO 27
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 27

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
                20                  25                  30
Pro Glu Glu Glu Glu Gly Gly Cys Glu Leu
            35                  40

<210> SEQ ID NO 28
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 28

Cys Trp Leu Thr Lys Lys Lys Tyr Ser Ser Ser Val His Asp Pro Asn
1               5                   10                  15
Gly Glu Tyr Met Phe Met Arg Ala Val Asn Thr Ala Lys Lys Ser Arg
                20                  25                  30
Leu Thr Asp Val Thr Leu
            35

<210> SEQ ID NO 29
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 29

Ala Leu Tyr Leu Leu Arg Arg Asp Gln Arg Leu Pro Pro Asp Ala His
1               5                   10                  15
Lys Pro Pro Gly Gly Gly Ser Phe Arg Thr Pro Ile Gln Glu Glu Gln

```
                    20                  25                  30

Ala Asp Ala His Ser Thr Leu Ala Lys Ile
        35                  40

<210> SEQ ID NO 30
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 30

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 31
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 31

Lys Ser Arg Gln Thr Pro Pro Leu Ala Ser Val Glu Met Glu Ala Met
1               5                   10                  15

Glu Ala Leu Pro Val Thr Trp Gly Thr Ser Ser Arg Asp Glu Asp Leu
            20                  25                  30

Glu Asn Cys Ser His His Leu
        35

<210> SEQ ID NO 32
<211> LENGTH: 194
<212> TYPE: PRT
<213> ORGANISM: Artificial Sequence
<220> FEATURE:
<223> OTHER INFORMATION: Synthetic polypeptide

<400> SEQUENCE: 32

Lys Arg Ile Lys Pro Ile Val Trp Pro Ser Leu Pro Asp His Lys Lys
1               5                   10                  15

Thr Leu Glu His Leu Cys Lys Lys Pro Arg Lys Asn Leu Asn Val Ser
            20                  25                  30

Phe Asn Pro Glu Ser Phe Leu Asp Cys Gln Ile His Arg Val Asp Asp
        35                  40                  45

Ile Gln Ala Arg Asp Glu Val Glu Gly Phe Leu Gln Asp Thr Phe Pro
    50                  55                  60

Gln Gln Leu Glu Glu Ser Glu Lys Gln Arg Leu Gly Gly Asp Val Gln
65                  70                  75                  80

Ser Pro Asn Cys Pro Ser Glu Asp Val Val Ile Thr Pro Glu Ser Phe
                85                  90                  95

Gly Arg Asp Ser Ser Leu Thr Cys Leu Ala Gly Asn Val Ser Ala Cys
            100                 105                 110

Asp Ala Pro Ile Leu Ser Ser Ser Arg Ser Leu Asp Cys Arg Glu Ser
        115                 120                 125

Gly Lys Asn Gly Pro His Val Tyr Gln Asp Leu Leu Leu Ser Leu Gly
    130                 135                 140
```

Thr Thr Asn Ser Thr Leu Pro Pro Phe Ser Leu Gln Ser Gly Ile
145                 150                 155                 160

Leu Thr Leu Asn Pro Val Ala Gln Gly Gln Pro Ile Leu Thr Ser Leu
                165                 170                 175

Gly Ser Asn Gln Glu Glu Ala Tyr Val Thr Met Ser Ser Phe Tyr Gln
            180                 185                 190

Asn Gln

<210> SEQ ID NO 33
<211> LENGTH: 416
<212> TYPE: PRT
<213> ORGANISM: Artificial Sequence
<220> FEATURE:
<223> OTHER INFORMATION: Synthetic polypeptide

<400> SEQUENCE: 33

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
                20                  25                  30

Glu Leu Phe Arg Pro His Met Ile Glu Asp Ile Gln Arg Ala Gly Ser
            35                  40                  45

Gly Ser Arg Arg Asp Gln Ala Arg Gln Leu Ile Asp Leu Glu Thr
50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
            325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
            355                 360                 365

Asp Ile Phe Glu Gln Trp Ala His Ser Glu Asp Leu Gln Ser Leu Leu
        370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 34
<211> LENGTH: 278
<212> TYPE: PRT
<213> ORGANISM: Artificial Sequence
<220> FEATURE:
<223> OTHER INFORMATION: Synthetic polypeptide

<400> SEQUENCE: 34

Val Gly Ala Leu Glu Ser Leu Arg Gly Asn Ala Asp Leu Ala Tyr Ile
1               5                   10                  15

Leu Ser Met Glu Pro Cys Gly His Cys Leu Ile Ile Asn Asn Val Asn
            20                  25                  30

Phe Cys Arg Glu Ser Gly Leu Arg Thr Arg Thr Gly Ser Asn Ile Asp
        35                  40                  45

Cys Glu Lys Leu Arg Arg Arg Phe Ser Ser Leu His Phe Met Val Glu
50                  55                  60

Val Lys Gly Asp Leu Thr Ala Lys Lys Met Val Leu Ala Leu Leu Glu
65                  70                  75                  80

Leu Ala Gln Gln Asp His Gly Ala Leu Asp Cys Cys Val Val Val Ile
            85                  90                  95

Leu Ser His Gly Cys Gln Ala Ser His Leu Gln Phe Pro Gly Ala Val
        100                 105                 110

Tyr Gly Thr Asp Gly Cys Pro Val Ser Val Glu Lys Ile Val Asn Ile
        115                 120                 125

Phe Asn Gly Thr Ser Cys Pro Ser Leu Gly Gly Lys Pro Lys Leu Phe
130                 135                 140

Phe Ile Gln Ala Cys Gly Gly Glu Gln Lys Asp His Gly Phe Glu Val
145                 150                 155                 160

Ala Ser Thr Ser Pro Glu Asp Glu Ser Pro Gly Ser Asn Pro Glu Pro
            165                 170                 175

Asp Ala Thr Pro Phe Gln Glu Gly Leu Arg Thr Phe Asp Gln Leu Asp
        180                 185                 190

Ala Ile Ser Ser Leu Pro Thr Pro Ser Asp Ile Phe Val Ser Tyr Ser
        195                 200                 205

Thr Phe Pro Gly Phe Val Ser Trp Arg Asp Pro Lys Ser Gly Ser Trp
210                 215                 220

Tyr Val Glu Thr Leu Asp Asp Ile Phe Glu Gln Trp Ala His Ser Glu
225                 230                 235                 240

Asp Leu Gln Ser Leu Leu Leu Arg Val Ala Asn Ala Val Ser Val Lys
            245                 250                 255

Gly Ile Tyr Lys Gln Met Pro Gly Cys Phe Asn Phe Leu Arg Lys Lys
            260                 265                 270

Leu Phe Phe Lys Thr Ser
        275

<210> SEQ ID NO 35
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 35

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 36
<211> LENGTH: 247
<212> TYPE: PRT
<213> ORGANISM: Artificial Sequence
<220> FEATURE:
<223> OTHER INFORMATION: Synthetic polypeptide

<400> SEQUENCE: 36

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Gly Ser Thr Ser Gly
            100                 105                 110

Ser Gly Lys Pro Gly Ser Ser Glu Gly Ser Thr Lys Gly Gln Val Gln
        115                 120                 125

Leu Gln Gln Ser Gly Ser Glu Leu Met Met Pro Gly Ala Ser Val Lys
    130                 135                 140

Ile Ser Cys Lys Ala Thr Gly Tyr Thr Phe Ser Asn Tyr Trp Ile Glu
145                 150                 155                 160

Trp Val Lys Gln Arg Pro Gly His Gly Leu Glu Trp Ile Gly Glu Ile
                165                 170                 175

```
Leu Pro Gly Thr Gly Arg Thr Ile Tyr Asn Glu Lys Phe Lys Gly Lys
            180                 185                 190

Ala Thr Phe Thr Ala Asp Ile Ser Ser Asn Thr Val Gln Met Gln Leu
        195                 200                 205

Ser Ser Leu Thr Ser Glu Asp Ser Ala Val Tyr Tyr Cys Ala Arg Arg
    210                 215                 220

Asp Tyr Tyr Gly Asn Phe Tyr Tyr Ala Met Asp Tyr Trp Gly Gln Gly
225                 230                 235                 240

Thr Ser Val Thr Val Ser Ser
                245

<210> SEQ ID NO 37
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 37

Gly Ser Thr Ser Gly Ser Gly Lys Pro Gly Ser Ser Glu Gly Ser Thr
1               5                   10                  15

Lys

<210> SEQ ID NO 38
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 38

Asp Ile Val Leu Thr Gln Ser Pro Ala Ser Leu Ala Val Ser Leu Gly
1               5                   10                  15

Asp Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Ser Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Gln Trp Val Arg Gln Ala Pro Gly Gln Gly Leu Glu Trp
                165                 170                 175

Met Gly Trp Ile Gln Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205
```

```
Tyr Leu Gln Ile Ser Ser Leu Lys Ala Glu Asp Thr Ala Val Tyr Tyr
    210                 215                 220

Cys Ala Leu Asp Tyr Ser Tyr Ala Met Asp Tyr Trp Gly Gln Gly Thr
225                 230                 235                 240

Leu Val Thr Val Ser Ser
                245
```

BI-SPECIFIC CHIMERIC ANTIGEN RECEPTOR AND USES THEREOF

RELATED APPLICATIONS

This application is a national stage filing under 35 U.S.C. § 371 of PCT International Application PCT/US2016/017219, filed Feb. 9, 2016, entitled "BI-SPECIFIC CHIMERIC ANTIGEN RECEPTOR AND USES THEREOF," which claims the benefit under 35.U.S.C. 119(e) of U.S. Provisional Application Ser. No. 62/114,045, filed Feb. 9, 2015, entitled "BI-SPECIFIC CHIMERIC ANTIGEN RECEPTOR AND USES THEREOF", and 62/121,862, filed Feb. 27, 2015, entitled "BI-SPECIFIC CHIMERIC ANTIGEN RECEPTOR AND USES THEREOF", the entire content of each of which is incorporated by reference herein.

BACKGROUND OF INVENTION

Multiple myeloma (MM) is an incurable plasma cell dyscrasia involving the bone marrow (BM), accounting for about 10% of all hematologic malignancies. With novel drugs and autologous stem cell transplantation, the average survival has significantly improved. Nevertheless, most patients experience resistant relapses and eventually succumb to their disease. Thus, there is an urgent need for more effective treatments.

SUMMARY OF THE INVENTION

Aspects of the invention relate to bi-specific CARs and methods of use thereof. In some embodiments, the CAR is expressed by a T cell and is useful for treatment of cancer, e.g., for treatment of multiple myeloma.

In some aspects, the disclosure provides chimeric antigen receptor (CAR) specific for CD138 and BCMA. In some embodiments, the CAR comprises a first single chain Fv (scFv) specific for CD138 and a second scFv specific for BCMA (e.g., connected by a linker). In some embodiments, the CAR comprises a dimer of polypeptides each comprising one or more (e.g., two or more) scFvs linked to one or more additional domains as described in this application.

In some embodiments, the CAR (e.g., one or both polypeptides of a CAR) further comprises a transmembrane domain. In some embodiments, the transmembrane domain is a CD28 transmembrane domain. In some embodiments, the transmembrane domain is a CD8 transmembrane domain. In some embodiments, the CAR (e.g., one or both polypeptides of a CAR) further comprises a co-stimulatory domain and/or a signaling domain. In some embodiments, the co-stimulatory domain is a 4-1BB co-stimulatory domain and/or the signaling domain is a CD27 signaling domain or a IL-15 receptor alpha signaling domain. In some embodiments, the CAR (e.g., one or both polypeptides of a CAR) comprises a signal transduction domain. In some embodiments, the signal transduction domain is a CD3zeta signal transduction domain. In some embodiments, the CAR (e.g., one or both polypeptides of a CAR) further comprises a CD28 extracellular domain.

In some embodiments, the CAR (e.g., one or both polypeptides of a CAR) further comprises one or more of a CD28 transmembrane domain, a 4-1BB co-stimulatory domain, a CD27 signaling domain, and a CD3zeta signal transduction domain. In some embodiments, the CAR (e.g., one or both polypeptides of a CAR) further comprises a caspase 9 functional domain and/or a mutated FK506 binding protein (FKBP) motif.

In some embodiments, the CAR is a homodimer comprising two polypeptides (e.g., two identical polypeptides), each polypeptide having a first single chain Fv (scFv) specific for CD138 and a second scFv specific for BCMA (e.g., connected by a linker). In some embodiments, the polypeptide (e.g., that is dimerized to form a homodimer) includes only two scFv domains (e.g., a first scFv specific for CD138 and a second scFv specific for BCMA) in addition to one or more other domains described herein. In some embodiments, the CAR is a heterodimer that comprises a first polypeptide and a second polypeptide, wherein the first polypeptide comprises the scFv specific for CD138 and the second polypeptide comprises the scFv specific for BCMA. In some embodiments, each polypeptide includes only one scFv (e.g., an scFv specific for CD138, or an scFv specific for BCMA) in addition to one or more other domains described herein. In some embodiments, each of the first and second polypeptide further comprises, independently, one or more of a transmembrane domain (e.g., a CD28 transmembrane domain), a co-stimulatory domain (e.g., a 4-1BB co-stimulatory domain), a signaling domain (e.g., a CD27 signaling domain) and a signal transduction domain (e.g., a CD3zeta signal transduction domain). In some embodiments, each of the first and second polypeptide further comprises, independently, a caspase 9 functional domain and/or a mutated FK506 binding protein (FKBP) motif. In some embodiments, the first and/or second polypeptide further comprise a CD28 extracellular domain.

Other aspects of the disclosure relate to a nucleic acid comprising a sequence that encodes a CAR (e.g., one or more polypeptides of a CAR) as described in any one of the above embodiments or as otherwise described herein. In some embodiments, one or more nucleic acids is provided comprising one or more sequences that encode a CAR as described in any one of the above embodiments or as otherwise described herein.

Yet other aspects of the disclosure relate to a lentiviral vector comprising a nucleic acid as described in any one of the above embodiments or as otherwise described herein. In some embodiments, one or more lentiviral vectors is provided comprising one or more nucleic acids as described in any one of the above embodiments or as otherwise described herein.

Other aspects of the disclosure relate to a cell comprising a CAR as described in any one of the above embodiments or as otherwise described herein. In some embodiments, the cell is a stem cell, NK cell, or T cell. In some embodiments, the cell is a T cell.

Other aspects of the disclosure relate to a composition comprising a plurality of a cell (e.g., a T cell) comprising a CAR as described in any one of the above embodiments or as otherwise described herein. In some embodiments, the composition further comprises a pharmaceutically acceptable carrier.

Yet other aspects of the disclosure relate to a method of generating a plurality of CAR modified cells, the method comprising introducing a lentiviral vector comprising a nucleic acid as described in any one of the above embodiments or as otherwise described herein into a plurality of immune cells. In some embodiments, one or more lentiviral vectors is provided comprising one or more nucleic acids in any one of the above embodiments or as otherwise described herein. In some embodiments, the immune cells are T cells.

Other aspects of the disclosure relate to a method of treating a subject having cancer or at risk of having cancer, the method comprising administering a T cell comprising a CAR as described in any one of the above embodiments or as otherwise described herein, a composition as described in any one of the above embodiments or as otherwise described herein, or a plurality of cells produced by a method as described in any one of the above embodiments or as otherwise described herein, into a subject having cancer or at risk of having cancer. In some embodiments, the cancer is multiple myeloma.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It should be appreciated that in greyscale versions of the drawings, GFP fluorescence appears as areas of lighter shading (e.g., white shading).

FIG. 2B is an illustration of rapid induction of apoptosis with the iCasp9 safety design in 4S CAR.

FIG. 3A is a table showing exemplary surface antigen expression profile for CS1, CD138, CD317 and BCMA in various multiple myeloma (MM) cell lines including Molp2, RPMI8226, and H929.

FIG. 3B is an exemplary representative flow cytometry analysis of CS1, CD138, CD317 and BCMA surface expression of an MM patient's bone marrow specimen stained with anti-CS1, anti-CD138, anti-CD317, and anti-BCMA antibodies.

FIG. 4E shows exemplary photographs taken after 8 days of killing with exemplary CARTs, where green Molp2 cells were observed under a microscope. FIG. 4F shows CART $2^{nd}$ round killing (day 2). After 12 days of killing, all targets were killed in the CS1, CD138 and BCMA groups. CART cells from $1^{st}$ round killing were set up in $2^{nd}$ killing using E/T=⅕ in 96 flat well plates. Molp2 remained in control no CART and 19z CART setting under microscope after 2 days in the $2^{nd}$ round of killing. In greyscale versions of the drawings, GFP fluorescence (e.g., green Molp2 cells) appears as areas of lighter shading (e.g., white shading).

FIG. 6A shows that CS1 and CD317 CARTs have more apoptotic cells compared to CD138 and BCMA CARTs.

FIG. 7A shows the percent of target cells remaining on Day 4 of coculture. Primary MM cells were labeled with CalceinAM and coculture was set up with the exemplar CARTs (E/T=1).

(FIG. 9A) After Day 1 killing, apoptotic target percentages. (FIG. 9B) Green target cells remaining after 1 day coculture. (FIG. 9C) After target cells were gone, more target cells were added to the remaining CART cells at E/T=⅓, FITC flow cytometry shows green target cells left in Day 1 after retargeting. In greyscale versions of the drawings, green target cells appear as areas of lighter shading (e.g., white shading).

FIGS. 10A and 10B are a series of exemplary flow cytometry graph, bar graph and GFP photos showing a short term and long term CART killing analysis. FIG. 10A shows 18 h FITC flow analysis of CART killing of MM cells. The result shows that the killing ability of the dual CART is similar to BCMA and better than CD138 CARTs; LJC PB, control T cells; CD123, CD123 CARTs; 40, CD138/BCMA dual CARTs. FIG. 10B shows GFP images of short term and long term killing. Dual CART and BCMA CART were more effective in short term killing than CD138 CARTs. Furthermore, Dual CARTs were the best among all three CARTs in long term killing assay. In greyscale versions of the drawings, GFP fluorescence appears as areas of lighter shading (e.g., white shading).

FIG. 10D are plots showing doubling time and cell number kinetics of CARTs after coculturing with target cells. Doubling time and growth potential of CARTs during target killing. The proliferation rate of the dual CARTs is similar to BCMA CARTs and better than CD138 CARTs.

DETAILED DESCRIPTION OF THE INVENTION

Figure 1A:
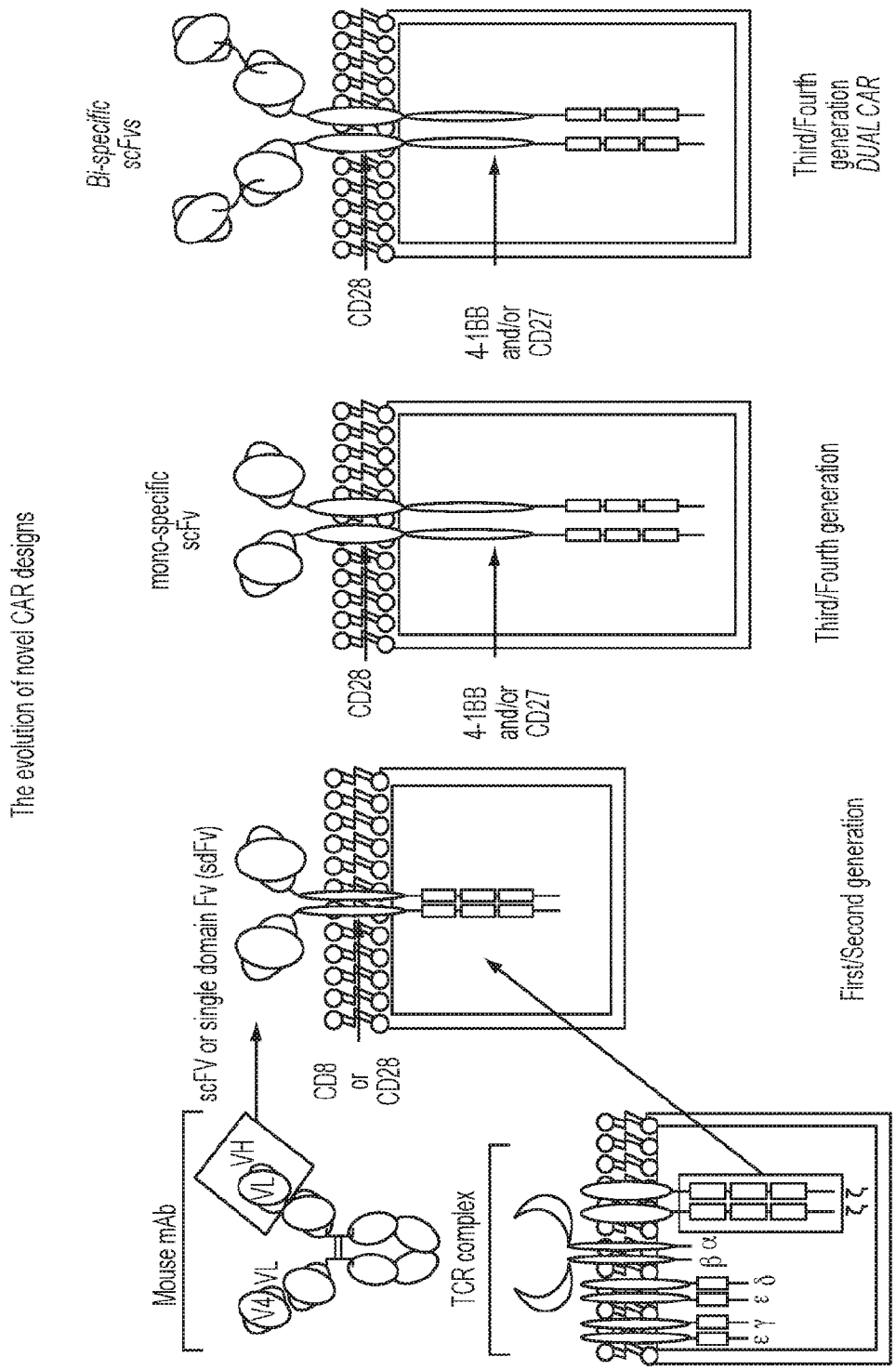
FIG. 1A is an illustration of exemplary CAR designs with the bi-specific CAR constructed in a $3^{rd}$ and $4^{th}$ generation of CAR backbone.

Chimeric antigen receptor (CAR) technology is an anti-cancer immune cell therapy approach aimed at generating the "magic bullet" of effector T cells to target specific tumor antigens. In general, CARTs are engineered T cells based on a single chain Fv (scFv) antibody moiety. In some embodiments, the chimeric antigen receptor (CAR) portion comprises a receptor complex that combines an antigen recognizing domain (e.g., scFv) and a signal transduction domain of T cells (such as including the CD3λ chain). The CART technology has evolved from the first-generation having only limited anti-tumor activities and in vivo survival ability, to the third generation that has improved target killing activity, and prolonged lifespan by the addition of co-stimulatory signals based on CD28 and 4-1BB. Further improvement can be made by incorporating a "suicide gene" to allow for rapid deletion of the infused CART cells in patients in the event of unexpected toxicity or when cancer eradication mission is accomplished.

As described herein, CARs were engineered based on scFvs against four different multiple myeloma (MM) antigens. The chimeric T cell receptor (TCR) motif contained a CD28 extracellular domain, CD28 transmembrane domain, 4-1BB co-stimulatory domain, CD27 intracellular domain and CD3zeta signal transduction domain. Lentiviral CAR vectors were used to infect Jurkat T cells and patient's T cells to generate CARTs. One CART tested, the dual CD138/BCMA CARTs displayed prolonged killing compared to the single CAR-Ts, and continued to be effective even after four rounds of MM-targeting co-cultures spanning >30 days.

Accordingly, aspects of the invention relate to bi-specific CARs and methods of use thereof. In some embodiments, the CAR is expressed by a T cell and is useful for treatment of cancer, e.g., for treatment of multiple myeloma.

In some embodiments, the CAR is specific for CD138 and BCMA. Syndecan-1 (CD138, also known as syndecan-1), a member of the transmembrane heparan sulfate proteoglycan family, acts as an extracellular matrix receptor 1,2 and is involved in many cellular functions, including cell-cell adhesion and cell-matrix adhesion. B cell maturation antigen (BCMA, also known as CD269 or TNFRSF17) is a member of the TNFR superfamily expressed on B cells. Exemplary, non-limiting human CD138 and BCMA sequences are provided below.

```
>gi|29568086|ref|NP_002988.3| syndecan-1
precursor [Homo sapiens]
                                    (SEQ ID NO: 1)
MRRAALWLWLCALALSLQPALPQIVATNLPPEDQDGSGDDSDNFSGSGA

GALQDITLSQQTPSTWKDTQLLTAIPTSPEPTGLEATAASTSTLPAGEG

PKEGEAVVLPEVEPGLTAREQEATPRPRETTQLPTTHQASTTTATTAQE

PATSHPHRDMQPGHHETSTPAGPSQADLHTPHTEDGGPSATERAAEDGA

SSQLPAAEGSGEQDFTFETSGENTAVVAVEPDRRNQSPVDQGATGASQG

LLDRKEVLGGVIAGGLVGLIFAVCLVGFMLYRMKKKDEGSYSLEEPKQA

NGGAYQKPTKQEEFYA

>gi|29568086:18-310 syndecan-1 mature protein
[Homo sapiens]
                                    (SEQ ID NO: 2)
QPALPQIVATNLPPEDQDGSGDDSDNFSGSGAGALQDITLSQQTPSTWK

DTQLLTAIPTSPEPTGLEATAASTSTLPAGEGPKEGEAVVLPEVEPGLT

AREQEATPRPRETTQLPTTHQASTTTATTAQEPATSHPHRDMQPGHHET

STPAGPSQADLHTPHTEDGGPSATERAAEDGASSQLPAAEGSGEQDFTF

ETSGENTAVVAVEPDRRNQSPVDQGATGASQGLLDRKEVLGGVIAGGLV

GLIFAVCLVGFMLYRMKKKDEGSYSLEEPKQANGGAYQKPTKQEEFYA
```

```
-continued
>gi|23238192|ref|NP_001183.2| tumor necrosis
factor receptor superfamily member 17, BCMA
[Homo sapiens]
                                    (SEQ ID NO: 3)
MLQMAGQCSQNEYFDSLLHACIPCQLRCSSNTPPLTCQRYCNASVTNSV

KGTNAILWTCLGLSLIISLAVFVLMFLLRKINSEPLKDEFKNTGSGLLG

MANIDLEKSRTGDEIILPRGLEYTVEECTCEDCIKSKPKVDSDHCFPLP

AMEEGATILVTTKTNDYCKSLPAALSATEIEKSISAR
```

In some embodiments, the CAR comprises a single chain Fv (scFv) specific for CD138 and a scFv specific for BCMA, which may be on a single polypeptide (e.g., connected by a linker) or on two polypeptides (e.g., one on a first CAR polypeptide and one a second CAR polypeptide, which may form a dimer once introduced into a cell).

In some embodiments, the CAR further comprises one or more of a CD28 extracellular domain, a CD28 or CD8 transmembrane domain, a 4-1BB co-stimulatory domain, a CD27 intracellular signaling domain and a CD3zeta signal transduction domain. In some embodiments, the arrangement of the CAR is selected from one of the following exemplary, non-limiting arrangements:
CD138scFV-BCMAscFV-CD28-(4-1BB)-CD27-CD3z
BCMAscFV-CD138scFV-CD28-(4-1BB)-CD27-CD3z
CD138scFV-BCMAscFV-CD8-CD27-CD3z
BCMAscFV-CD138scFV-CD8-CD27-CD3z
CD138scFV-BCMAscFV-CD8-CD27-IL-15Ra-CD3z
BCMAscFV-CD138scFV-CD8-CD27-IL-15Ra-CD3z
CD138scFV-BCMAscFV-CD28-CD27-IL-15Ra-CD3z
BCMAscFV-CD138scFV-CD28-CD27-IL-15Ra-CD3z
CD138scFV-BCMAscFV-CD28-(4-1BB)-CD27-IL15Ra-CD3z
BCMAscFV-CD138scFV-CD28-(4-1BB)-CD27-IL15Ra-CD3z In some embodiments, the above exemplary, non-limiting arrangements are from left to right, N-terminus to C-terminus of the CAR.

In some embodiments, the CAR further comprises one or more of a CD28 extracellular domain, a CD28 transmembrane domain, a 4-1BB co-stimulatory domain, a CD27 intracellular signaling domain, a CD3zeta signal transduction domain, a caspase 9 functional domain and a mutated FK506 binding protein (FKBP) motif.

In some embodiments, the CAR is a homodimer comprising two polypeptides, each polypeptide having a first single chain Fv (scFv) specific for CD138 and a second scFv specific for BCMA (e.g., connected by a linker). Each of the two polypeptides may further comprise one or more of a CD28 transmembrane domain, a 4-1BB co-stimulatory domain CD27 signaling domain, and a CD3zeta signal transduction domain. In some embodiments, the two polypeptides comprise a CD28 transmembrane domain, a 4-1BB co-stimulatory domain CD27 signaling domain, a CD3zeta signal transduction domain, a caspase 9 functional domain and a mutated FK506 binding protein (FKBP) motif. In some embodiments, the CAR is a heterodimer that comprises a first polypeptide and a second polypeptide, wherein the first polypeptide comprises a scFv specific for CD138 and the second polypeptide comprises a scFv specific for BCMA. Each of the first and second polypeptide may further comprise, independently, one or more of a CD28 transmembrane domain, a 4-1BB co-stimulatory domain, CD27 signaling domain, and a CD3zeta signal transduction domain. In some embodiments, each of the first and second polypeptide may further comprise, independently, a CD28 transmembrane domain, a 4-1BB co-stimulatory domain, a CD27 signaling domain, a CD3zeta signal transduction domain, a caspase 9 functional domain and a mutated FK506 binding protein (FKBP) motif.

The CAR may also include several hinge elements and/or spacer sequences (such as between individual domain elements). In some embodiments, the spacer comprises one or more repeats of a GGGS (SEQ ID NO: 4), GGGGS (SEQ ID NO: 5), GS18 (GSTSGGGSGGGSGGGSS) (SEQ ID NO: 6), GS8 (GGGGSGGG) (SEQ ID NO: 7) or 218S linker (GSTSGSGKPGSSEGSTKG) (SEQ ID NO: 8) sequence. Other exemplary spacer sequences include GGGGS (SEQ ID NO: 5), GGGGSGGGS (SEQ ID NO: 9), (GGGGS)x3 (SEQ ID NO:10), GSTSGGGSGGGSGGGSS (SEQ ID NO: 6), GSTSGSGKPGSSEGSTKG (SEQ ID NO: 8), GGGGSGGG (SEQ ID NO: 7), VEPKSCDKTHTCPPCP (SEQ ID NO: 11), LDPKSSDKTHTCPPCP (SEQ ID NO: 12), VEPKSPDKTHTCPPCP (SEQ ID NO: 13), or LDKTHTCPPCP (SEQ ID NO: 14).

In some embodiments, the first and/or second polypeptide further comprises, independently, one or more of a CD8a hinge, a CD137 signaling domain, or a CD27 signaling domain. In some embodiments, the two polypeptides have the same or different transmembrane domains, the same or different co-stimulatory domains, and/or the same or different (e.g., complementary) signal transduction domains.

In some embodiments, the CAR of the invention comprises an extracellular domain having an antigen recognition domain, a transmembrane domain, and a multi-functional cytoplasmic domain. In some embodiments, the CAR can comprise a fully human antibody or antibody fragment. In some embodiments, the transmembrane domain that naturally is associated with one of the domains in the CAR is used. In some embodiments, the transmembrane domain can be selected or modified by amino acid substitution to avoid binding of such domains to the transmembrane domains of the same or different surface membrane proteins to minimize interactions with other members of the receptor complex.

In some embodiments, the CAR T cells of the invention can be generated by introducing a lentiviral vector comprising a desired CAR targeting two antigens (e.g., CD138 and BCMA), which may comprise a single polypeptide targeting both antigens (e.g., CD138 and BCMA) or a first polypeptide targeting a first antigen (e.g., CD138) and a second polypeptide targeting a second antigen (e.g., BCMA) into the cells. For example, the lentiviral vector comprises a CAR comprising a tumor antigen binding domain (e.g., CD138 or BCMA), optionally a CD8a hinge, a transmembrane domain, and one or more signaling domains, into the cells.

In some embodiments, the CAR T cells of the invention can be generated by transfecting an RNA encoding the desired CAR, into the cells. In some embodiments, the CAR is transiently expressed in the genetically modified CAR T cells.

In some embodiments, the invention relates to administering a genetically modified T cell expressing a CAR for the treatment of a patient having cancer or at risk of having cancer, such as multiple myeloma.

Exemplary Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies, human antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, kappa and lambda light chains refer to the two major antibody light chain isotypes.

By the term "synthetic antibody" as used herein, is meant an antibody which is generated using recombinant DNA technology, such as, for example, an antibody expressed by a lentiviral vector as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

In some embodiments, the term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "tumor antigen" as used herein refers to an antigen associated with a cancer cell, such as a multiple myeloma cell. Examples of tumor antigens include but are not limited CD138 and BCMA.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species. "Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, the cancer is a cancer that expresses CD138 and/or BCMA. Exemplary cancers that express CD138 and/or BCMA include multiple myeloma and Hodgkin's lymphoma. In some embodiments, cancer refers to multiple myeloma. Multiple myeloma is a cancer of plasma cells. Multiple myeloma can be diagnosed with blood tests (serum protein electrophoresis, serum free kappa/lambda light chain assay), bone marrow examination, urine protein electrophoresis, and/or X-rays of commonly involved bones. In some embodiments, cancer refers to Hodgkin's lymphoma (HL). HL is a cancer of B cells.

An "effective amount" as used herein, means an amount which provides a therapeutic or prophylactic benefit.

As used herein, the term "exogenous" refers to any material introduced from or produced outside an organism, cell, tissue or system.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lenti viruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lenti viruses. Vectors derived from lenti viruses offer the means to achieve significant levels of gene transfer in vivo, ex vivo or in vitro.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Codon-optimized" means that codons relating to a specific amino acid are optimized for translational efficiency of a gene of interest. Codon optimization typically involves evaluating the gene or sequence of interest and substituting the codon with a more prevalent or common codon used for the same amino acid in a specific cell or species. Programs used by those in the art to evaluate codon optimization include those provided by Integrated DNA Technologies, EnCor Biotechnology, Inc., JCat, OptimumGene™ (GenScript USA, Inc., Pisataway, N.J. 08854), etc. The sequences encoding the CAR embodiments described herein may be codon-optimized, which can increase their translational efficiency.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" or "overexpression" is intended to indicate an abnormal level of expression (e.g., of the tumor antigen) in a cell from a disease area (e.g., a solid tumor within a specific tissue or organ of the patient) relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In some embodiments, the patient, subject or individual is a human.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds" or "specific for", as used herein with respect to an antibody (such as a scFv), is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). Examples of subjects include humans, dogs, cats, mice, rats, and transgenic species thereof.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Compositions

In some aspects, the present invention provides a chimeric antigen receptor (CAR) specific for CD138 and BCMA. In some embodiments the CAR comprises an antigen-binding domain specific for CD138, an antigen-binding domain specific for BCMA, an extracellular domain, a transmembrane domain and an intracellular domain. In some embodiments, the antigen-binding domain for CD138 and the antigen-binding domain for BCMA are fused together, e.g., using a linker or spacer as described herein, to form a single polypeptide chain. In some embodiments, the CAR is a homodimer. In some embodiments the CAR is a heterodimer that comprises a first polypeptide comprising an antigen-binding domain specific for CD138, a first extracellular domain, a first transmembrane domain, and a first intracellular domain; and a second polypeptide comprising an antigen-binding domain specific for BCMA, a second extracellular domain, a second transmembrane domain, and a second intracellular domain. In some embodiments, the CAR of the invention is fully humanized. In some embodiments, the intracellular domain or otherwise the cytoplasmic domain comprises a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

In some embodiments, between the extracellular domain and the transmembrane domain of the CAR, or between the cytoplasmic domain and the transmembrane domain of the CAR, or between the antigen-binding domain for CD138 and the antigen-binding domain for BCMA, there may be incorporated a spacer or hinge domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, 10 to 100 amino acids, 10 to 30 amino acids, or 5 to 20 amino acids. It also should be appreciated that one or more spacer domains may be included in other regions of a CAR, as aspects of the disclosure are not limited in this respect.

In some embodiments, the spacer and/or hinge sequences of the CAR are selected from one or more of the following exemplary sequences:

```
Exemplary Spacers:
                                            (SEQ ID NO: 5)
GGGGS (SEQ ID NO: 9)
GGGGSGGGGS (SEQ ID NO: 10)
GGGGS x3

GS18:
                                            (SEQ ID NO: 6)
GSTSGGGSGGGSGGGGSS

218S:
                                            (SEQ ID NO: 8)
GSTSGSGKPGSSEGSTKG

GS8:
                                            (SEQ ID NO: 7)
GGGGSGGG (SEQ ID NO: 4)
GGGS

Exemplary Hinges:
Native:
                                            (SEQ ID NO: 11)
VEPKSCDKTHTCPPCP C233S:
                                            (SEQ ID NO: 12)
LDPKSSDKTHTCPPCP C233P:
                                            (SEQ ID NO: 13)
VEPKSPDKTHTCPPCP
```

```
-continued
Delta5:
                                            (SEQ ID NO: 14)
LDKTHTCPPCP
```

Antigen Binding Domains

In some embodiments, the CAR of the invention comprises at least two target-specific binding elements otherwise referred to as an antigen binding moieties or antigen binding domains. In some embodiments, the CAR of the invention can be engineered to target a tumor antigen of interest by way of engineering a desired antigen binding moiety that specifically binds to an antigen on a tumor cell. In some embodiments, the antigen binding domains are N-terminus of to a transmembrane domain and/or intracellular domain of a CAR as described herein.

Each antigen binding domain of the CAR may target, for example, CD138, hm1.24 (CD317), CS-1 or mature B cell marker BCMA.

The antigen binding domain can be any domain that binds to the antigen including but not limited to monoclonal antibodies, scFvs, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domains of the CAR to comprise a human antibody or fragment thereof. Thus, in some embodiments, the antigen binding domain portion comprises a human antibody or a fragment thereof. For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO91/10741; each of which is incorporated herein by reference in its entirety. A human antibody can also be an antibody wherein the heavy and light chains are encoded by a nucleotide sequence derived from one or more sources of human DNA. Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Antibodies directed against an antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For a detailed discussion of this technology for producing human antibodies and human monoclonal antibodies and protocols for producing such antibodies, see, e.g., PCT Publication Nos. WO2014/055771, WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. A "humanized" antibody retains a similar antigenic specificity as the original antibody, i.e., in the present invention, the ability to bind, for example, CD138 or BCMA.

In some embodiments, a first antigen binding moiety portion of the CAR of the invention targets CD138 and a second antigen binding moiety portion of the CAR of the invention targets BCMA. In some embodiments, the first antigen binding moiety portion in the CAR of the invention is a fully human anti-CD138 scFv and the second antigen binding moiety portion in the CAR of the invention is a fully human anti-BCMA scFv.

An exemplary CD138 scFV is provided below. The CDRs are shown by underlines.

```
Heavy Chain (VH) (SEQ ID NO: 15):
QVQLQQSGSELMMPGASVKIS (CDR1)
CKATGYTFSNYWIE

WVKQRPGHGLEWIG (CDR2)
EILPGTGRTIYNE (CDR3)
KFKGKATFTADISSNTVQMQLSSLTSEDSAVYYCAR

RDYYGNFYYAMDY

WGQGTSVTVSS

Light Chain (VL) (SEQ ID NO: 16):
DIQMTQSTSSLSASLGDRVTISC (CDR1)
SASQGINNYLN

WYQQKPDGTVELLIY (CDR2)
YTSTLQS (CDR3)
GVPSRFSGSGSGTDYSLTISNLEPEDIGTYYCQQ

YSKLPRT

FGGGTKLEIK
```

An exemplary BCMA scFv is provided below. The CDRs are shown by underlines.

```
Heavy Chain (VH) (SEQ ID NO: 17):
QVQLVQSGSELKKPGASVKVSCKASGYTFT (CDR1)
DYSIQ

WVRQAPGQGLEWMG (CDR2)
WIQTETREPAYAYDFRG

RFVFSLDTSVSTAYLQISSLKAEDTAVYYC (CDR3)
ALDYSYAMDY

WGQGTLVTVSS

Light Chain (VL) (SEQ ID NO: 18):
DIVLTQSPASLAVSLGDRATINC (CDR1)
RASESVSVIGAHLIH

WYQQKPGQPPKLLIY (CDR2)
LASNLET

GVPARFSGSGSGTDFTLTISSLQAEDAAIYYC (CDR3)
LQSRIFPRT

FGQGTKLEIK
```

In some embodiments, the heavy chain (VH) and light chain (VL) of a scFV (e.g., a CD138 scFV or a BCMA scFV) are joined as a single polypeptide chain by a linker molecule (e.g., a 218S linker), and can be joined to one or more additional domains in a single polypeptide (e.g., that can dimerize to form a homodimeric or heterodimeric CAR) as described in this application (e.g., via one or more additional linkers, for example, one or more additional 218S linkers).

Leader Domain

In some embodiments, a CAR is designed with a leader domain for directing the translated chimeric protein to the membrane. The leader domain is generally in the range of 15 to 30 amino acids. Examples of the leader domain include CD8a leader (21 amino acids), CD33 leader (17 amino acids), CD4 leader (25 amino acids), IL-2R (CD25) leader (21 amino acids), trypsinogen-2 leader (15 amino acids), VEGFR1 leader (26 amino acids), EGFR leader (24 amino acids) and GMCSFR leader (22 amino acids).

Extracellular Domain

In some embodiments, a CAR is designed with an extracellular T cell co-stimulatory domain such as CD28 extracellular domain. The extracellular domain may serve as a hinge domain or T cell activation domain. Examples include the CD28 extracellular domain, which has 50 amino acids. An exemplary sequence of the CD28 extracellular domain is:

```
                                          (SEQ ID NO: 19)
YVNQTDIYFCKIEVMYPPPYLDNEKSNGTIIHVKGKHLCPSPLFPGPSKP
```

Transmembrane Domain

In some embodiments, the CAR comprises a transmembrane domain. In some embodiments, the CAR can be designed to comprise a transmembrane domain that is fused to the extracellular domain of the CAR. In some embodiments, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane domains of particular use in this invention may be derived from (e.g., comprise at least the transmembrane domain(s) of) the alpha, beta or zeta chain of the T-cell receptor, CD28, CD3 epsilon, CD3, CD45, CD4, CD5, CD8, CD9, CD16, CD22, CD25, CD33, CD37, CD64, CD80, CD86, CD134, CD137, or CD154. Transmembrane domains can be identified using any method known in the art or described herein, e.g., by using the UniProt Database.

In some embodiments, the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, e.g., between 2 and 10 amino acids in length may form the linkage between the transmembrane domain and the cytoplasmic signaling domain of the CAR. A glycine-serine doublet provides an exemplary suitable linker.

In some embodiments, the transmembrane domain in the CAR of the invention is the CD8 transmembrane domain. Sequences of CD8 for this purposes are taught in PCT pub no. WO2014/055771, which is incorporated by reference herein.

In some embodiments, the transmembrane domain in the CAR of the invention is the CD28 transmembrane domain. Exemplary sequences are below. One skilled in the art would appreciate that the full transmembrane domain, or portion thereof, is implemented with the cytoplasmic domain, or a portion thereof. Typically, the transmembrane and cytoplasmic domains used would be contiguous portions of the CD28 sequence. In some embodiments, the CD28 transmembrane domain comprises the exemplary transmembrane domain sequence below, or a fragment or variant thereof that is capable of anchoring a CAR comprising the sequence to a cell membrane.

```
CD28 (amino acids 19-220)
                                      (SEQ ID NO: 20)
NKILVKQSPMLVAYDNAVNLSCKYSYNLFSREFRASLHKGLDSAVEVCVV

YGNYSQQLQVYSKTGFNCDGKLGNESVTFYLQNLYVNQTDIYFCKIEVMY

PPPYLDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAAY

RS

CD28 (amino acids 153-179, transmembrane domain)
                                      (SEQ ID NO: 21)
FWVLVVVGGVLACYSLLVTVAFIIFWV
```

In some embodiments, the CAR of the invention is comprises a region of CD28 that contains all or part of an extracellular domain, all or part of a transmembrane domain and all or part of a cytoplasmic domain. An exemplary sequence of a region of CD28 for inclusion in a CAR is provided below. In some embodiments, the CD28 transmembrane domain comprises the exemplary transmembrane domain sequence below, or a fragment or variant thereof that is capable of anchoring a CAR comprising the sequence to a cell membrane.

```
CD28 region
                                      (SEQ ID NO: 22)
IEVMYPPPYLDNEKSNGTIIHVKGKHLCPSPLFPGPSKPFWVLVVVGGV
LACYSLLVTVAFIIFWVRSKRSRLLHSDYMNMTPRRPGPTRKHYQPYAP
PRDFAAYRSAS
```

In some embodiments, the transmembrane domain of the CAR of the invention comprises a hinge domain such as a CD8 hinge domain. An exemplary CD8 hinge domain sequence is provided below. In some embodiments, the CD8 hinge domain comprises the exemplary sequence below, or a fragment or variant thereof that is capable of providing flexibility to or preventing steric hindrance of the CAR or the domain(s) attached to the hinge domain. In some instances, the transmembrane domain of the CAR of the invention comprises the CD8 hinge domain. In some embodiments, a hinge domain between a scFv and a transmembrane domain provides flexibility to the chimeric molecule and may prevent steric hindrance to the scFv binding function. See PCT pub No. WO2014/055771, which teaches an exemplary sequence, which is incorporated by reference herein. An exemplary CD8 hinge domain sequence is provided below.

```
CD8 hinge domain
                                      (SEQ ID NO: 23)
AKPTTTPAPRPPTPAPTIASQPLSLRPEACRPAAGGAVHTRGLDFACD
```

Intracellular Domain

In some embodiments, the intracellular domain (also referred to herein as an cytoplasmic domain or intracellular signaling domain) of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire domain. To the extent that a truncated portion of the intracellular signaling domain is used, such truncated portion may be used in place of the intact domain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any fragment or variant of these sequences and any synthetic sequence that has the same functional capability.

It is known that signals generated through the endogenous TCR alone are insufficient for full activation of the T cell and that a secondary or co-stimulatory signal is also required. Thus, T cell activation can be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from 4-1BB, OX40, ICOS, CD21, CD27, TCR zeta, FcR gamma, FcR beta, CD3 gamma, CD3 delta, CD3 epsilon, CD5, CD22, CD79a, CD79b, and CD66d. In some embodiments, the cytoplasmic signaling molecule in the CAR of the invention comprises a signal transduction domain sequence derived from CD3 zeta. Exemplary CD3 zeta domain sequences are provided below. In some embodiments, the CD3zeta signal transduction domain comprises one of the exemplary sequences, or a fragment or variant thereof that, when included in a CAR, has the same or an improved function (such as cytolytic activity or secretion of cytokines) compared to a CAR comprising the exemplary sequence below. The function may be tested using a method provided herein, such as the method provided in Example 1 or Example 2.

CD3 Zeta Signal Transduction Domain—
Example 1

(SEQ ID NO: 24)
RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR

CD3 Zeta Signal Transduction Domain—
Example 2

(SEQ ID NO: 25)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR

The cytoplasmic domain of the CAR can be designed to comprise the CD3-zeta signal transduction domain by itself or combined with any other desired cytoplasmic domain(s) useful in the context of the CAR of the invention, such as a 4-1BB co-stimulatory domain, CD27 signaling domain and/ or a CD28 transmembrane domain. For example, the cytoplasmic domain of the CAR can comprise a CD3 zeta chain portion and a costimulatory signaling region. The costimulatory signaling region refers to a portion of the CAR comprising the intracellular domain of a costimulatory molecule. Thus, while the invention in exemplified primarily with 4-1BB, CD28, IL-15Ra, ICOS, OX40, CD27 and CD127 as the co-stimulatory or signaling element(s), other additional costimulatory or signaling elements are within the scope of the invention. Exemplary sequences of co-stimulatory and intracellular domains are shown below. Other exemplary 4-1BB co-stimulatory domains are described in US Patent Publication US20050113564, which is incorporated by reference herein. See, e.g., SEQ ID NO:2 of US20050113564, which is incorporated by reference herein.

CD28 cytoplasmic domain:
(SEQ ID NO: 26)
RSKRSRLLHSDYMNMTPRRPGPTRKHYQPYAPPRDFAAYRS 4-1BB (CD137) intracellular TRAF binding domain:
(SEQ ID NO: 27)
KRGRKKLLYIFKQPFMRPVQTTQEEDGCSCRFPEEEEGGCEL ICOS intracellular domain:
(SEQ ID NO: 28)
CWLTKKKYSSSVHDPNGEYMFMRAVNTAKKSRLTDVTL OX40 intracellular domain:
(SEQ ID NO: 29)
ALYLLRRDQRLPPDAHKPPGGGSFRTPIQEEQADAHSTLAKI CD27 intracellular domain:
(SEQ ID NO: 30)
QRRKYRSNKGESPVEPAEPCHYSCPREEEGSTIPIQEDYRKPEPACSP IL-15Ra intracellular domain:
(SEQ ID NO: 31)
KSRQTPPLASVEMEAMEALPVTWGTSSRDEDLENCSHHL CD127 intracellular domain:
(SEQ ID NO: 32)
KRIKPIVWPSLPDHKKTLEHLCKKPRKNLNVSFNPESFLDCQIHRVDDIQ

ARDEVEGFLQDTFPQQLEESEKQRLGGDVQSPNCPSEDVVITPESFGRDS

SLTCLAGNVSACDAPILSSSRSLDCRESGKNGPHVYQDLLLSLGTTNSTL

PPPFSLQSGILTLNPVAQGQPILTSLGSNQEEAYVTMSSFYQNQ

In some embodiments, a CAR of the invention comprises the apoptosis inducing gene Casp9 or a domain or truncated version thereof. An exemplary Casp9 sequence and truncated sequence is below. In some embodiments, the CAR comprises a 2A peptide linker between a CD3 zeta domain and Casp9.

CASP9 amino acid sequence
(SEQ ID NO: 33)
MDEADRRLLRRCRLRLVEELQVDQLWDALLSRELFRPHMIEDIQRAGSG

SRRDQARQLIIDLETRGSQALPLFISCLEDTGQDMLASFLRTNRQAAKL

SKPTLENLTPVVLRPEIRKPEVLRPETPRPVDIGSGGFGDVGALESLRG

NADLAYILSMEPCGHCLIINNVNFCRESGLRTRTGSNIDCEKLRRRFSS

LHFMVEVKGDLTAKKMVLALLELAQQDHGALDCCVVVILSHGCQASHLQ

FPGAVYGTDGCPVSVEKIVNIFNGTSCPSLGGKPKLFFIQACGGEQKDH

GFEVASTSPEDESPGSNPEPDATPFQEGLRTFDQLDAISSLPTPSDIFV

SYSTFPGFVSWRDPKSGSWYVETLDDIFEQWAHSEDLQSLLLRVANAVS

VKGIYKQMPGCFNFLRKKLFFKTS

A truncated CASP9 amino acid sequence
(SEQ ID NO: 34)
VGALESLRGNADLAYILSMEPCGHCLIINNVNFCRESGLRTRTGSNIDC

EKLRRRFSSLHFMVEVKGDLTAKKMVLALLELAQQDHGALDCCVVVILS

HGCQASHLQFPGAVYGTDGCPVSVEKIVNIFNGTSCPSLGGKPKLFFIQ

ACGGEQKDHGFEVASTSPEDESPGSNPEPDATPFQEGLRTFDQLDAISS

LPTPSDIFVSYSTFPGFVSWRDPKSGSWYVETLDDIFEQWAHSEDLQSL

LLRVANAVSVKGIYKQMPGCFNFLRKKLFFKTS

In some embodiments, the CAR further comprises a mutated FK506 binding protein (e.g., FKBPf36v) motif. An exemplary mutated FK506 binding protein motif is provided below.

FKBP f36v amino acid sequence:
(SEQ ID NO: 35)
MGVQVETISPGDGRTFPKRGQTCVVHYTGMLEDGKKVDSSRDRNKPFKF
MLGKQEVIRGWEEGVAQMSVGQRAKLTISPDYAYGATGHPGIIPPHATL
VFDVELLKLE The cytoplasmic signaling sequences within the cytoplasmic signaling portion of the CAR of the invention may be linked to each other in a random or specified order. Optionally, a short oligo- or polypeptide linker or spacer, preferably between 5 and 20 amino acids in length may form the linkage, e.g., be inserted between cytoplasmic domains. A GGGGS (SEQ ID NO: 5) or (GGGGS)x3 (SEQ ID NO: 10) provides a particularly suitable linker.

In some embodiments, the cytoplasmic domain is designed to comprise a signaling domain of CD3-zeta, a 4-1BB co-stimulatory domain, a CD27 intracellular domain, and a transmembrane domain of CD28. In some instances, the CAR can further comprise the apoptosis inducing gene Casp9.

Vectors

In some embodiments, the present invention encompasses a DNA construct comprising sequences of a CAR, wherein the sequence comprises the nucleic acid sequence that encodes one or more antigen binding moieties (e.g., a CD138 moiety and a BCMA moiety) operably linked to the nucleic acid sequence encoding one or more of an extracellular domain, a transmembrane domain, and an intracellular domain. In some embodiments, the DNA construct encodes a CAR having an arrangement selected from one of the following exemplary, non-limiting arrangements:

CD138scFV-BCMAscFV-CD28-(4-1BB)-CD27-CD3z
BCMAscFV-CD138scFV-CD28-(4-1BB)-CD27-CD3z
CD138scFV-BCMAscFV-CD8-CD27-CD3z
BCMAscFV-CD138scFV-CD8-CD27-CD3z
CD138scFV-BCMAscFV-CD8-CD27-IL-15Ra-CD3z
BCMAscFV-CD138scFV-CD8-CD27-IL-15Ra-CD3z
CD138scFV-BCMAscFV-CD28-CD27-IL-15Ra-CD3z
BCMAscFV-CD138scFV-CD28-CD27-IL-15Ra-CD3z
CD138scFV-BCMAscFV-CD28-(4-1BB)-CD27-IL15Ra-CD3z
BCMAscFV-CD138scFV-CD28-(4-1BB)-CD27-IL15Ra-CD3z

In some embodiments, the above exemplary, non-limiting arrangements are from left to right, N-terminus to C-terminus of the CAR.

In some embodiments, two DNA constructs are contemplated, one DNA construct comprising the nucleic acid sequence encoding an antigen binding moiety specific for CD138 operably linked to the nucleic acid sequence encoding one or more of an extracellular domain, a transmembrane domain, and an intracellular domain and a second DNA construct comprising the nucleic acid sequence encoding an antigen binding moiety specific for BCMA operably linked to the nucleic acid sequence encoding one or more of an extracellular domain, a transmembrane domain, and an intracellular domain. An exemplary intracellular domain that can be used in the CAR of the invention includes but is not limited to the intracellular domain(s) of CD3-zeta, CD28, CD127, CD27, 4-1BB and the like. The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lenti viral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transposons.

In brief summary, the expression of natural or synthetic nucleic acids encoding CARs (e.g., encoding a polypeptide that can dimerize to form a homodimeric CAR, or encoding two different polypeptides that can dimerize to form a heterodimeric CAR) is typically achieved by operably linking a nucleic acid encoding the CAR polypeptide or portions thereof to a promoter, and incorporating the construct into an expression vector. In some embodiments, two expression vectors may be used, e.g., one expression vector comprising a CD138 CAR construct and a second expression vector comprising a BCMA CAR construct. The vectors can be suitable for replication and integration into eukaryotes. Typical cloning vectors contain transcription and translation terminators, initiation sequences, and promoters useful for regulation of the expression of the desired nucleic acid sequence. The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector. The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. A number of retrovirus vectors are known in the art. In some embodiments, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, the promoter is a EF-1a promoter.

In order to assess the expression of a CAR polypeptide or portions thereof, the expression vector(s) to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic resistance genes, such as neo and the like. Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, antibiotic resistance or fluorescence. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially.

In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector(s), the vector(s) can be readily introduced into a host cell, e.g., mammalian, bacterial, yeast, or insect cell by any method in the art. For example, the expression vector(s) can be transferred into a host cell by physical, chemical, or biological means. In some embodiments, the host cell is a T cell. Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In some embodiments, the genetically modified T cells of the invention are modified through the introduction of RNA (e.g., an mRNA comprises a sequence encoding a CAR as described herein). In some embodiments, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, one template for the RNA CAR comprises an extracellular domain comprising an anti-CD138 scFv and an anti-BCMA scFV; a transmembrane domain (such as the transmembrane domain of CD28); and a cytoplasmic domain that comprises the signaling domain of CD3-zeta and the signaling domain of 4-1BB, CD27, CD127 or a combination thereof. For example, another template for the RNA CAR comprises an extracellular domain comprising an anti-CD138 scFv; a transmembrane domain (such as the transmembrane domain of CD28); and a cytoplasmic domain that comprises the signaling domain of CD3-zeta and the signaling domain of 4-1BB, CD27, CD127 or a combination thereof. For example, another template for the RNA CAR comprises an extracellular domain comprising an anti-BCMA scFv; a transmembrane domain (such as the transmembrane domain of CD28); and a cytoplasmic domain that comprises the signaling domain of CD3-zeta and the signaling domain of 4-1BB, CD27, CD127 or a combination thereof.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified Immune Cells

In some embodiments, the CAR sequence(s) (e.g., nucleic acid sequence(s) encoding a CAR as described herein) are delivered into cells (e.g., T cells, stem cells, or NK cells) using a retroviral or lentiviral vector. In some embodiments, the arrangement of the elements of the CAR encoded by the CAR sequence(s) is selected from one of the following exemplary, non-limiting arrangements:

CD138scFV-BCMAscFV-CD28-(4-1BB)-CD27-CD3z
BCMAscFV-CD138scFV-CD28-(4-1BB)-CD27-CD3z
CD138scFV-BCMAscFV-CD8-CD27-CD3z
BCMAscFV-CD138scFV-CD8-CD27-CD3z
CD138scFV-BCMAscFV-CD8-CD27-IL-15Ra-CD3z
BCMAscFV-CD138scFV-CD8-CD27-IL-15Ra-CD3z
CD138scFV-BCMAscFV-CD28-CD27-IL-15Ra-CD3z
BCMAscFV-CD138scFV-CD28-CD27-IL-15Ra-CD3z
CD138scFV-BCMAscFV-CD28-(4-1BB)-CD27-IL15Ra-CD3z
BCMAscFV-CD138scFV-CD28-(4-1BB)-CD27-IL15Ra-CD3z

In some embodiments, the above exemplary, non-limiting arrangements are from left to right, N-terminus to C-terminus of the CAR.

CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient In another embodiment, the desired CAR can be expressed in the cells (e.g., T cells or NK cells) by way of transponsons.

The disclosed methods can be applied to the modulation of immune cell (e.g., T cell or NK cell) activity in basic research and therapy, in the fields of cancer, stem cells, acute and chronic infections, and autoimmune diseases, including the assessment of the ability of the genetically modified T cell or NK cell to kill a target cell, e.g., a target cancer cell. vector, making it possible to individually regulate the expression level. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

Cloning of cells is not necessary because of the efficiency of transduction of the CAR with lentiviral vectors or onco-retroviral vectors, which can stably and uniformly modify the entire lymphocyte population.

Sources of Immune Cells

Prior to expansion and genetic modification of the immune cells (e.g., T cells) of the invention, a source of immune cells (e.g., T cells) is obtained from a subject. Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. The immune cells (e.g., T cells) may also be generated from induced pluripotent stem cells or hematopoietic stem cells or progenitor cells. In some embodiments of the present invention, any number of immune cell lines, including but not limited to T cell and NK cell lines, available in the art, may be used. In some embodiments of the present invention, immune cells (e.g., T cells) can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, NK cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, immune cells (e.g., T cells) are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$.

Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of $CD8^+$T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than CD8+ T cells in dilute concentrations. In some embodiments, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In some embodiments a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In some embodiments, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In some embodiments, a ratio of particles to cells of 1:1 or less is used. In one particular embodiment, a preferred particle:cell ratio is 1:5. In further embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In some embodiments the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in some embodiments, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments of the present invention, the mixture may be cultured for several hours (about 3 hours) to about 14 days or any hourly integer value in between. In another embodiment, the mixture may be cultured for 21 days. In some embodiments of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFp, and TNF-a or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (¾, CD4$^+$) that is greater than the cytotoxic or suppressor T cell population ($T_c$, CD8$^+$). Ex vivo expansion of T cells by stimulating CD3 and CD28 receptors produces a population of T cells that prior to about days 8-9 consists predominately of ¾ cells, while after about days 8-9, the population of T cells comprises an increasingly greater population of Tc cells. Accordingly, depending on the purpose of treatment, infusing a subject with a T cell population comprising predominately of $T_H$ cells may be advantageous. Similarly, if an antigen-specific subset of Tc cells has been isolated it may be beneficial to expand this subset to a greater degree.

Further, in addition to CD4 and CD 8 markers, other phenotypic markers vary significantly, but in large part, reproducibly during the course of the cell expansion process. Thus, such reproducibility enables the ability to tailor an activated T cell product for specific purposes.

Therapeutic Application

In some embodiments, the present invention encompasses a cell (e.g., T cell) modified to express a CAR that combines antigen recognition domain(s) (e.g., an scFv specific for CD138 and another scFv for BCMA) with one or more of an extracellular domain (e.g., a CD28 extracellular domain), a transmembrane domain (e.g., a CD28 or CD8 transmembrane domain) and an intracellular domain (e.g., an intracellular domain of CD3-zeta, CD28, CD27, 4-1BB, or any combinations thereof). Therefore, in some instances, the transduced immune cell (e.g., T cell) can elicit a CAR-mediated immune (e.g., T-cell) response. In some embodiments, the invention provides the use of a CAR to redirect the specificity of a primary T cell to a tumor antigen. Thus, in some embodiments, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target (e.g., CD138 and BCMA), a zeta chain portion comprising for example the intracellular domain of human CD3-zeta, and a costimulatory signaling region. In some embodiments, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, CD138 and BCMA-specific CAR T cells elicit an immune response specific against cells expressing CD138 and/or BCMA. While the data disclosed herein specifically disclose lentiviral vectors comprising anti-CD138 scFv, anti-BCMA scFv, a CD28 extracellular domain, a CD28 transmembrane domain, and 4-1BB, CD27 and CD3-zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer. In some embodiments, the antigen bind moiety portion of the CAR of the invention is designed to treat a particular cancer, such as multiple myeloma.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells. Ex vivo procedures are well known in the art and are discussed more fully below. Briefly, cells are isolated from a mammal (preferably a human) and genetically modified (e.g., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells. In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised, such as individuals having cancer. In particular, the CAR-modified T cells of the invention are used in the treatment of multiple myeloma. In certain embodiments, the cells of the invention are used in the treatment of patients at risk for developing multiple myeloma.

The CAR-modified immune cells (e.g., CAR T cells) of the present invention may be administered either alone, or as a composition (e.g., a pharmaceutical composition) in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants {e.g., aluminum hydroxide); and preservatives.

Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the CAR-modified immune cells (e.g., CAR T cells) described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated immune (e.g., T cells) to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the immune cell (e.g., T cell) compositions of the present invention are administered to a patient by intradermal or subcutaneous injection. In another embodiment, the immune cell (e.g., T cell) compositions of the present invention are preferably administered by i.v. injection. The compositions of immune cells (e.g., T cells) may be injected directly into a tumor, lymph node, or site of disease.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766). Strategies for CAR T cell dosing and scheduling have been discussed (Ertl et al, 2011, Cancer Res, 71:3175-81; Junghans, 2010, Journal of Translational Medicine, 8:55).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Dual CAR for Treatment of Multiple Myeloma

Multiple myeloma (MM) is an incurable plasma cell dyscrasia involving the bone marrow (BM), accounting for about 10% of all hematologic malignancies. With novel drugs and autologous stem cell transplantation, the average survival has significantly improved. Nevertheless, most patients experience resistant relapses and eventually succumb to their disease. Thus, there is an urgent need for more effective treatments. Targeted CAR-T cells that can completely eradicate residual MM cells might be a highly effective immunotherapy strategy for MM patients.

Materials and Methods:

Lenti-CAR vectors targeting several known MM surface antigens-CS1, CD317 (hm1.24), CD138, and B cell maturation antigen (BCMA, CD269 or TNFRSF17)-were generated. MM patients' BM and peripheral blood T cells were transduced with these lenti-CAR vectors, and killing efficacy was assessed in short term and long term co-incubation experiments by flow cytometry using green fluorescent protein-labeled MM cells and annexin V/PI staining.

Results:

Patients' T cells transduced with the above four lenti-CARs displayed similar MM-specific killing activities when co-cultured 1:1 with Molp2 MM cell line. All four CAR-Ts killed >70% of MM cells after 24 hr, with CS1 and BCMA CARs showing the highest killing (>80%). After 72 hr, all MM cells were killed. Then ten times more MM cells were added to the CAR-T cultures to examine continued killing effect. Except for CD317 CAR-Ts, all other MM-specific CAR-Ts displayed complete killing effect in the 2nd round of 5-day co-cultures. Primary MM cells from two previously treated patients were also tested, and similar killing effect from these CAR-Ts was observed. It was observed that CS1 and CD317 CARs resulted in self-killing of these CAR-Ts. Expression of these antigens on the surface of T cells was confirmed. The latter explains the self-killing as well as the limitations of these specific CAR-Ts, and renders these targets less suitable for clinical application. As a result, a novel dual CD138/BCMA CAR was engineered and examined its functionality in targeting MM cells. The results demonstrated that the dual CD138/BCMA CAR-Ts displayed prolonged killing compared to the single CAR-Ts, and continued to be effective even after four rounds of MM-targeting co-cultures spanning >30 days.

Example 2: MM-Specific Dual CD138/BCMA CAR-Ts

CAR technology is a novel anti-cancer immune cell therapy approach aimed at generating the "magic bullet" of effector T cells to target specific tumor antigens. CARTs are engineered T cells based on a single chain Fv (scFv) antibody moiety. The chimeric antigen receptor (CAR) portion is consisted of a receptor complex that combines an antigen recognizing domain (scFv) and a signal transduction domain of T cells (usually the CD3λ chain). The CART technology has evolved from the first-generation having only limited anti-tumor activities and in vivo survival ability, to the third generation that has improved target killing activity, and prolonged lifespan by the addition of co-stimulatory signals based on CD28 and 4-1BB. Further improvement can be made by incorporating a "suicide gene" to allow for rapid deletion of the infused CART cells in patients in the event of unexpected toxicity or when cancer eradication mission is accomplished.

In this study, novel CARs were engineered based on scFvs against four different MM antigens. The chimeric T cell receptor (TCR) motif contained a CD28 extracellular domain, a CD28 transmembrane domain, a 4-1BB co-stimulatory domain, a CD27 signaling domain, and CD3zeta signal transduction domain. Lentiviral CAR vectors were used to infect Jurkat T cells and patient's T cells to generate CARTs.

To prevent tumor escape from T cells with only single antigen specificity, four well-studied MM antigens were identified as CAR targets: CD138, hm1.24 (CD317), CS-1 and mature B cell marker BCMA. The combination CAR approach aims to target MM with high specificity. Nevertheless, the potential non-specific killing of normal tissues may have severe side effects. To increase safety, a fourth generation CAR which includes a self-destructive design has been established. The 4th generation safety CARs were constructed as a fusion protein containing a truncated caspase 9 functional domain and a mutated FK506 binding protein (FKBP) motif. These fourth generation safety CARs are transferred into primary human T cells including MM patients' bone marrow T cells for functional evaluation.

Figure 1B:
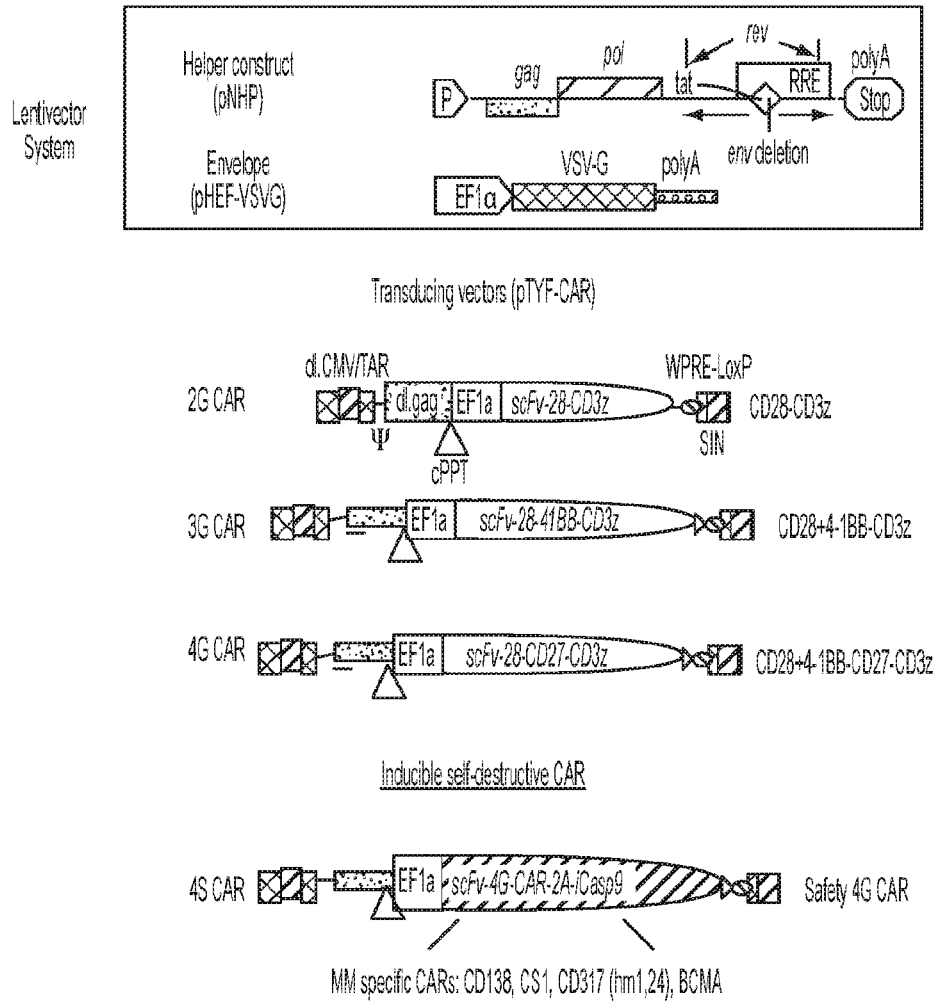
FIG. 1B are diagrams showing a series of exemplary Lentiviral CAR engineering, including the structure for second (2G), third (3G), fourth (4G) generation CARs, and 4G with an inducible caspase 9 gene safety design (4S).
Figure 2A:
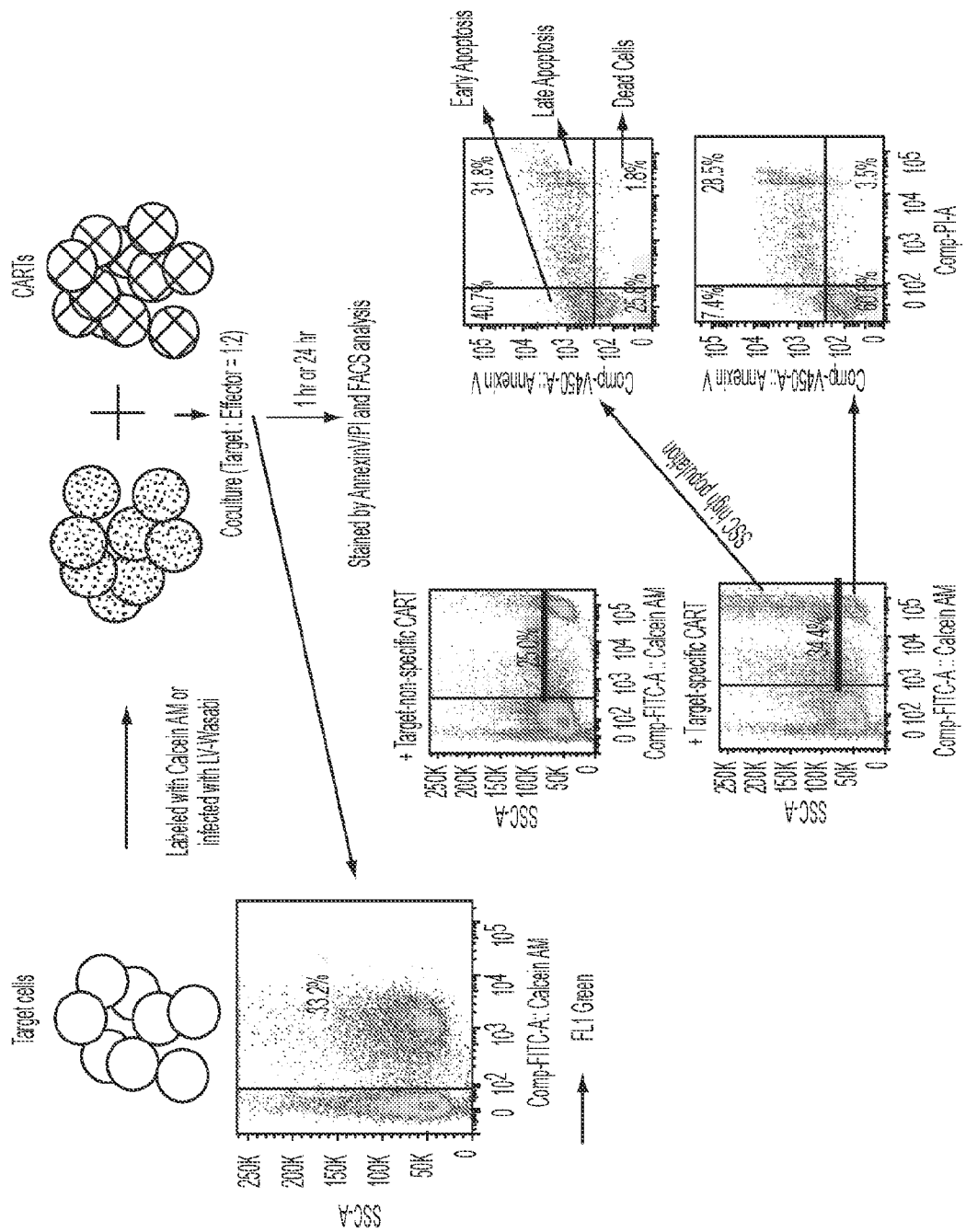
FIG. 2A is an illustration of exemplary CAR T cell target killing and flow cytometry analysis of target cell death.
Figure 4A:
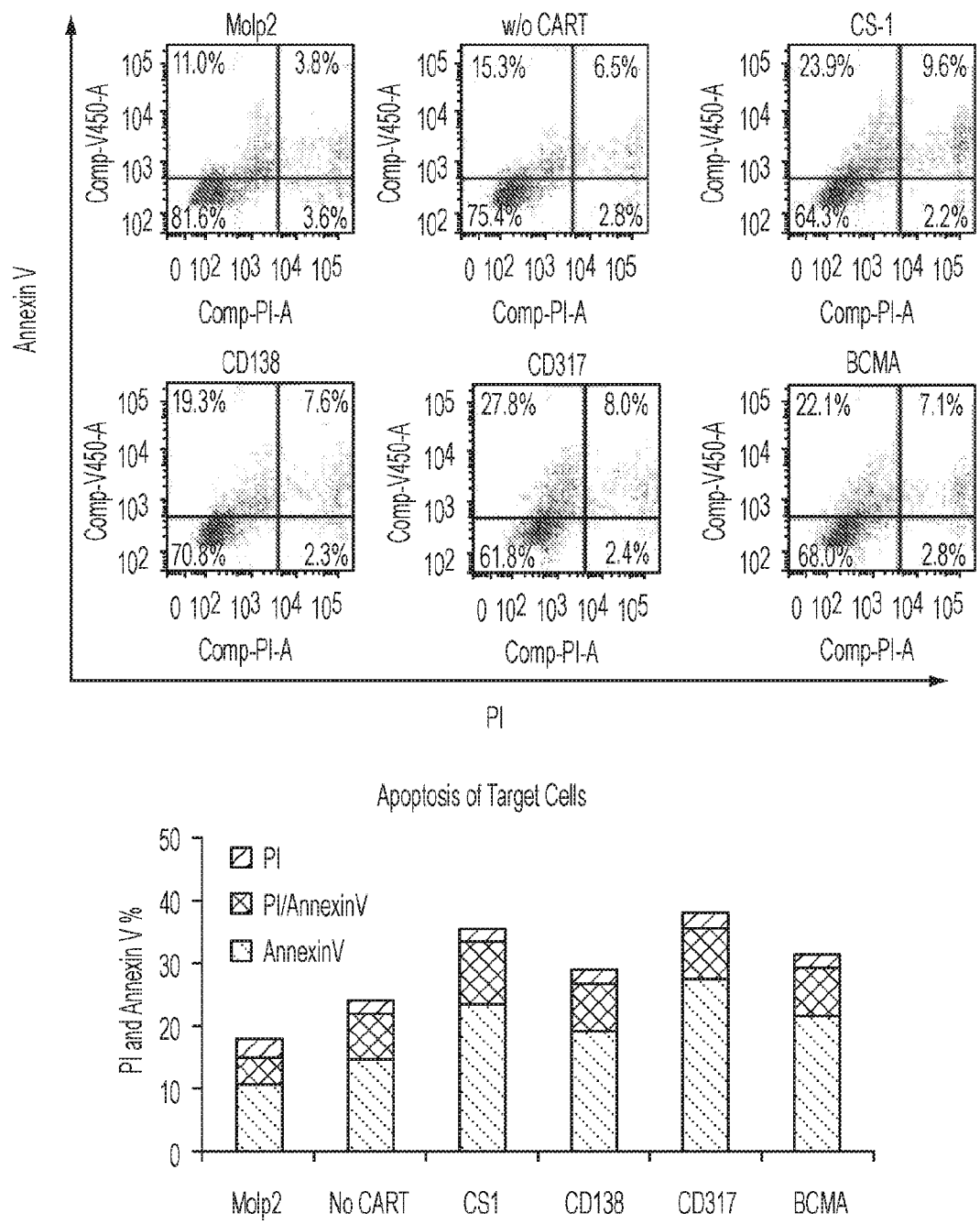
FIG. 4A is a series of exemplary plots showing Annexin V and PI staining of Molp2 coculturing with different CARTs of an one to one ratio and an exemplary bar graph of late apoptosis percentage.
Figure 4B:
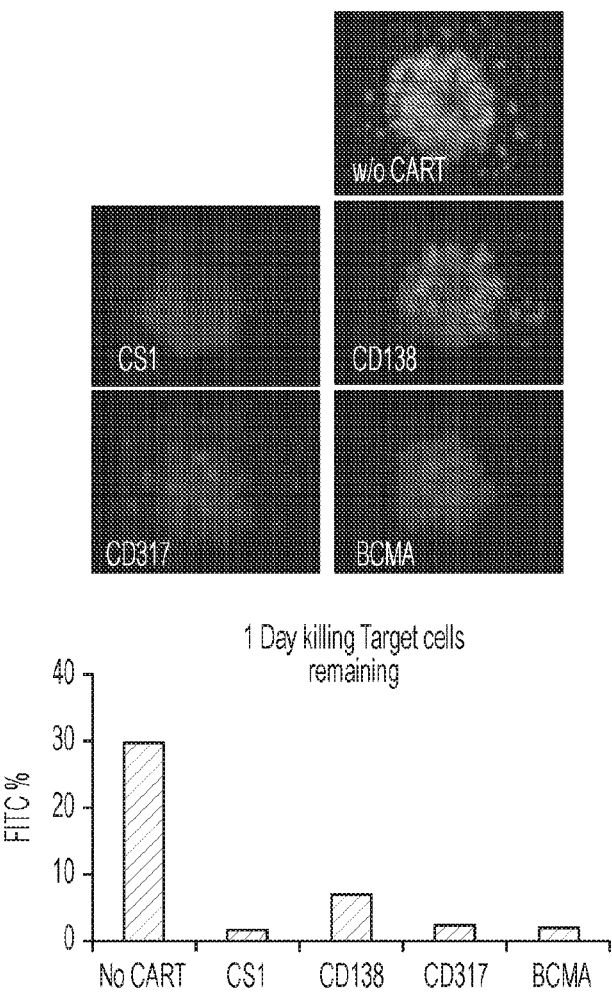
FIG. 4B is a series of exemplary photographs and a graph showing FITC+ target cell percentage.
Figure 4C:
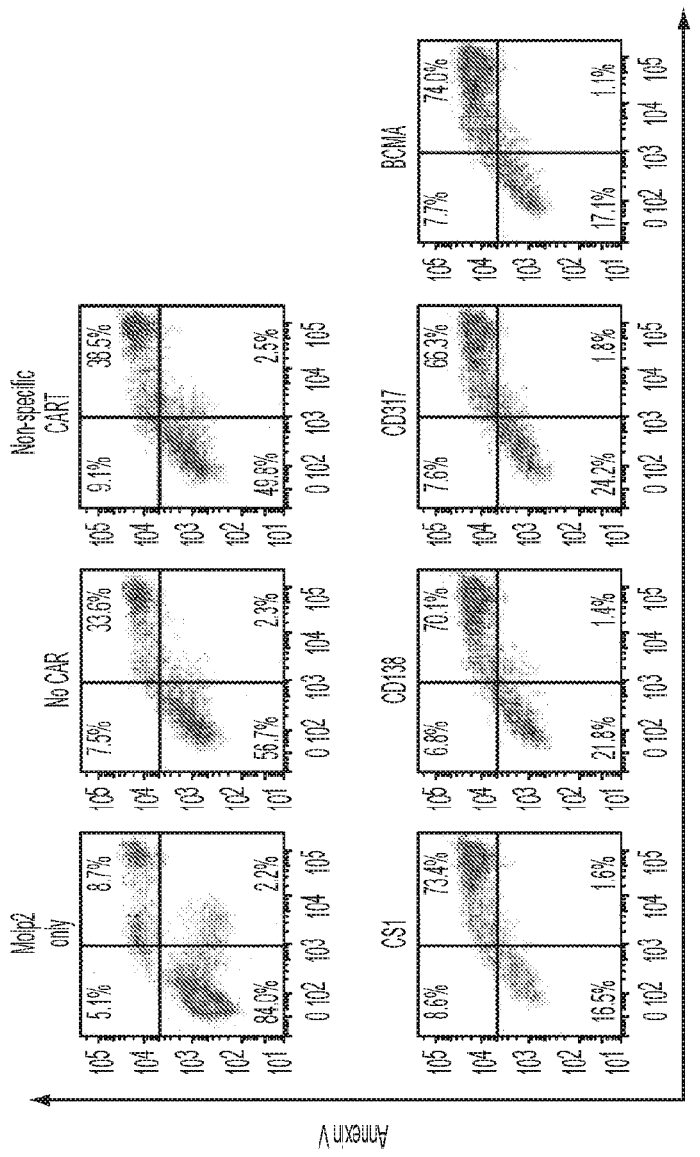
FIG. 4C is a series of FACS plots showing apoptotic target cells. MM CARTs were co-cultured with Molp2 expressing GFP in 96 U-shaped wells with an effector-to-target ration of 1 (E/T=1). After 1 day, cells were stained with PI and annexin V to define dead target cells.
Figure 4D:
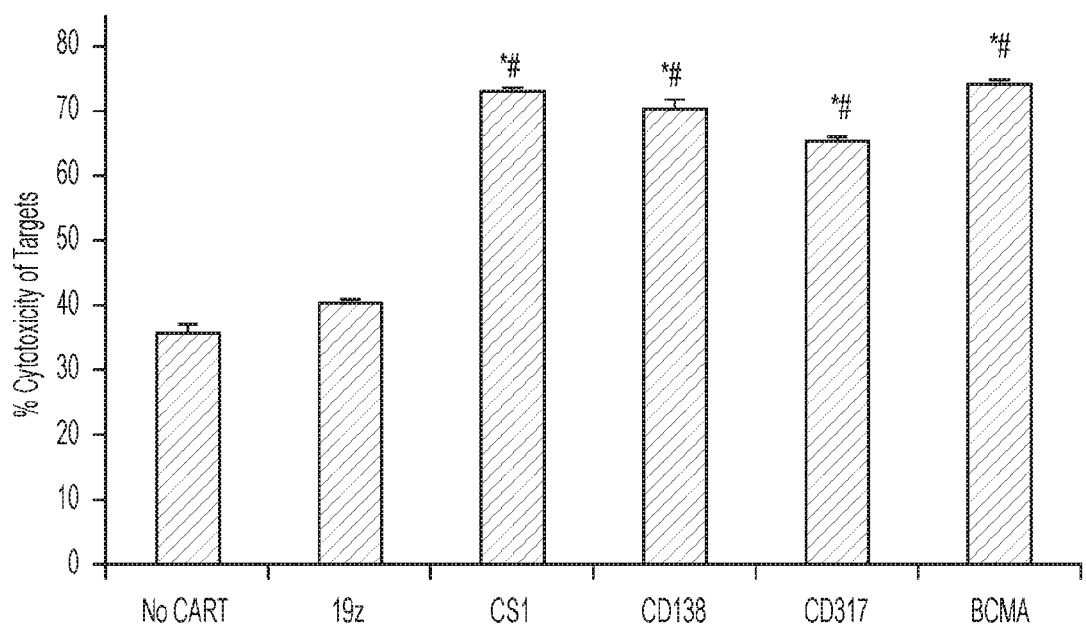
FIG. 4D is an exemplary graph showing the percentage of cytotoxicity of target cells treated with different exemplary CARTs. *P<0.05 compared to no CART, #=P<0.05 compared to 19z CART.
Figure 4E:
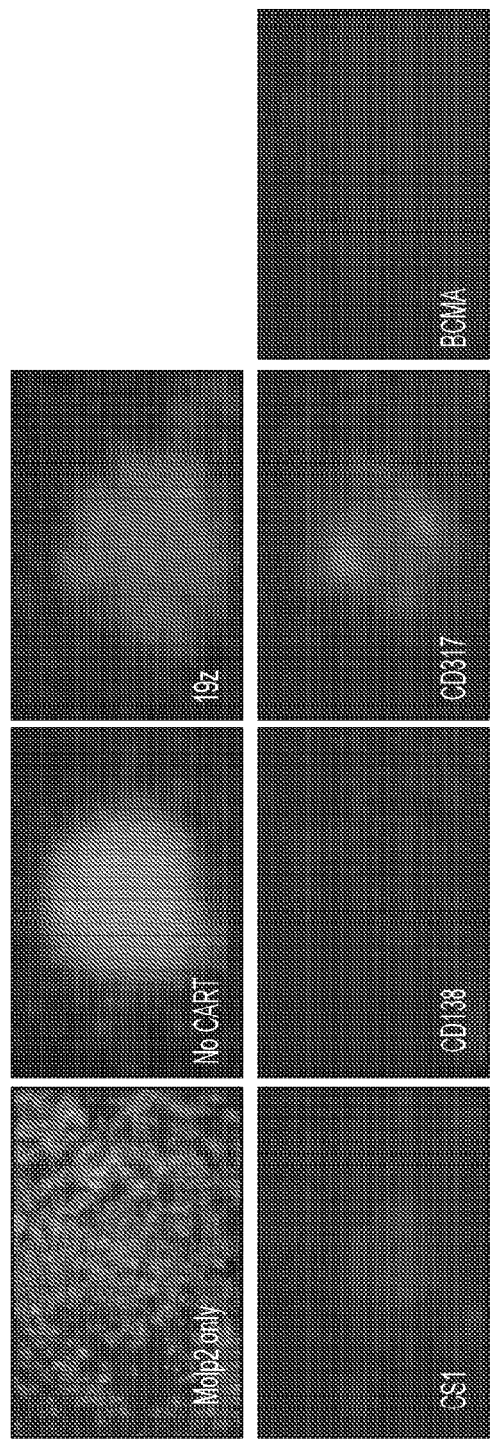
FIGS. 4E and 4F are exemplary GFP photos taken by fluorescence microscope during coculture showing killing of target cells.
Figure 4F:
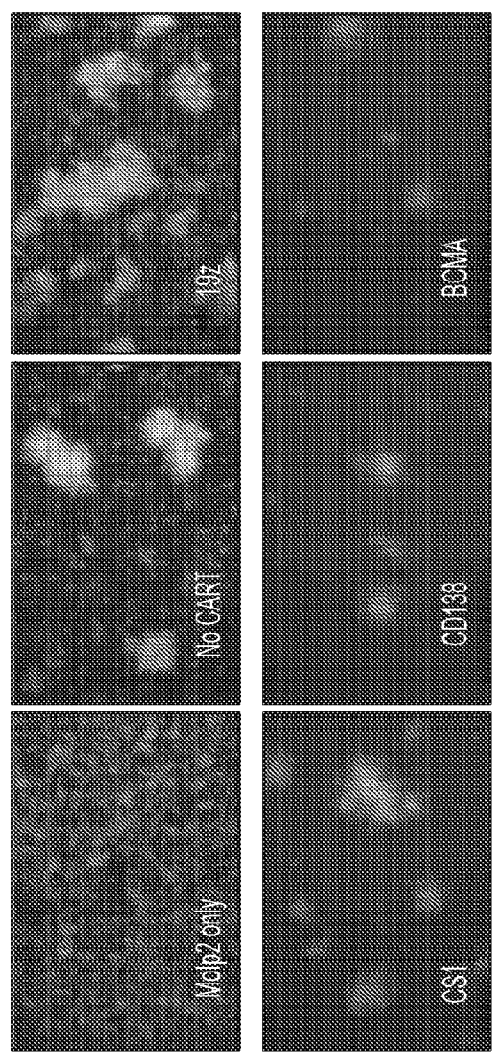

Methods:

Lentiviral CAR Engineering, Target Killing and Self-Destruction Illustration:

Non-limiting embodiments of lenti-CARs are illustrated in FIGS. 1A and 1B. Control Hela-tCD19 cells were established based on a cytoplasmic domain-truncated CD19 cDNA. HeLa-tCD19 cells were cocultured with non-specific and CD19-specific Jurkat (Jurkat-CAR-19Z) and 2 hours later analyzed by flow cytometry. HeLa cells infected with the self-destructive iCasp9 CAR lentivector were rapidly killed after the addition of AP1903, a FKBP dimer forming inducer (FIGS. 2A and B).

The Dual CAR Design:

An scFV specific for CD138 was conjugated to an scFv for BCMA through a 218S linker. The sequence of the full dual antigen-binding domain is shown below and is broken up by each subdomain.

CD138 scFv (SEQ ID NO: 36)
DIQMTQSTSSLSASLGDRVTISCSASQGINNYLNWYQQKPDGTVELLIYY

TSTLQSGVPSRFSGSGSGTDYSLTISNLEPEDIGTYYCQQYSKLPRTFGG

GTKLEIKGSTSGSGKPGSSEGSTKGQVQLQQSGSELMMPGASVKISCKAT

GYTFSNYWIEWVKQRPGHGLEWIGEILPGTGRTIYNEKFKGKATFTADIS

SNTVQMQLSSLTSEDSAVYYCARRDYYGNFYYAMDYWGQGTSVTVSS

-continued 218S linker
(SEQ ID NO: 37)
GSTSGSGKPGSSEGSTK

BCMA scFv
(SEQ ID NO: 38)
DIVLTQSPASLAVSLGDRATINCRASESVSVIGAHLIHWYQQKPGQPPKLL

IYLASNLETGVPARFSGSGSGTDFTLTISSLQAEDAAIYYCLQSRIFPRTF

GQGTKLEIKGSTSGSGKPGSSEGSTKGQVQLVQSGSELKKPGASVKVSCKA

SGYTFTDYSIQWVRQAPGQGLEWMGWIQTETREPAYAYDFRGRFVFSLDTS

VSTAYLQISSLKAEDTAVYYCALDYSYAMDYWGQGTLVTVSS

The dual scFvs were fused with a human IgG Fc and a bi-specific CD138/BCMA-IgG gene was then generated and cloned into lentivector. The lentivector was used to infect CHO cells and supernatant IgG was collected from the infected CHO cell culture and used for MM cell surface antigen staining. A second sheep antihuman Ig-FITC was used before flow cytometry analysis.

A Rapid Target Killing Assay by FACS:

Ag-specific target cells were labeled with green fluorescence (Calcein AM dye or Wasabi gene) and co-cultured with CART cells (target:effector=1:1) for 1 hour. The cells were stained with Annexin-V and PI and analyzed by flow cytometry. CART-targeted killing was recorded by quantitative analysis of the shifted side scattered (SSC) population (orange yellow circles), and early and late apoptotic and PI-stained (dead) cells were enumerated.

Follow Up Observation of Killing Assay:

GFP FACS analysis and photo taken by fluorescence microscope are used for short term and long term observation of different killing ability of each Ag-specific CART.

Results:

FIGS. 4A-F show Annexin V and PI staining of Molp2 coculturing with different CARTs of an one to one ratio and bar graph of late apoptosis percentage. Four CARTs with different Ag-specificity exerted similar killing function toward MM cell line Molp2. CS-1 and BCMA had the best killing ability in 24 hrs with over 80% cell death observed. After 8-day coculture, except for CD317, all CARTs completely killed Molp2. CD317 was eliminated in second round killing, of which the number of Molp2 is ten times more than first round. Killing effect of three CARTs are observed with CS-1 CART being the least effective.

Figure 6A:
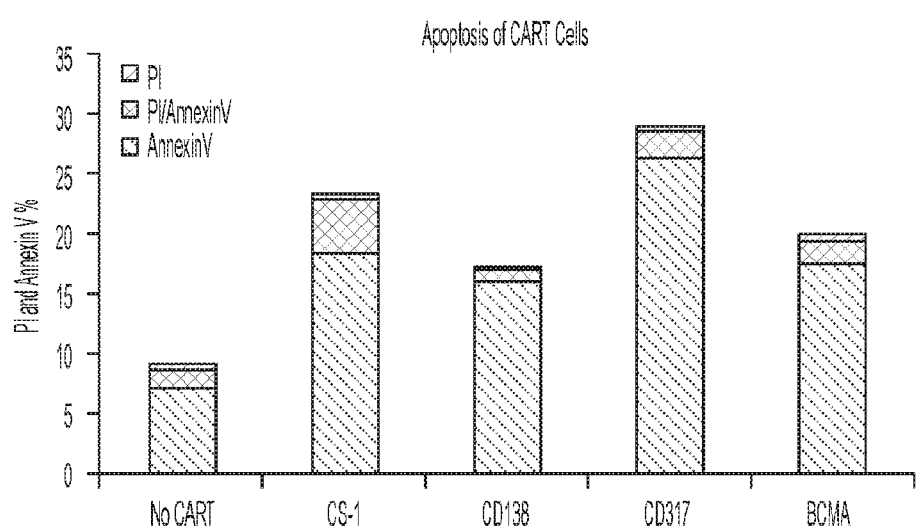
FIGS. 6A and B are a series of exemplary plots of apoptotic CARTs and surface staining of CS-1 and CD317 expression on patient bone marrow T cells.
Figure 6B:
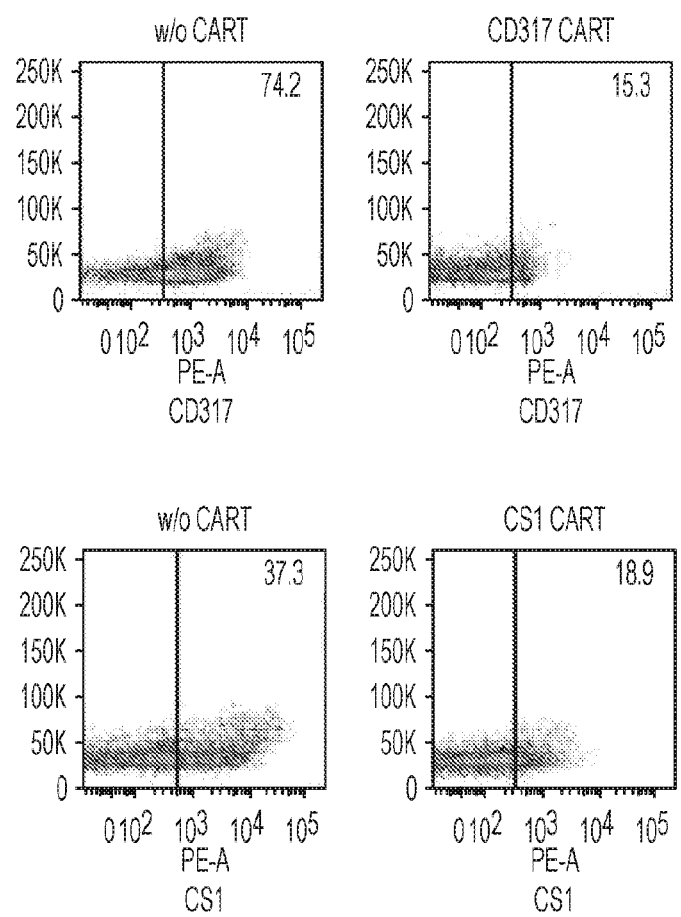
FIG. 6B shows that after 2 days in culture, the CD317 expression in CD317 CARTs was decreased, and likewise, CS1 CARTs displayed reduced CS1 expression.

FIG. 6 shows surface staining of CS-1 and CD317 expression on patient bone marrow T cells. CS-1 and CD317 were found to be extensively expressed on patient T cells. Cell number and the percentage of annexin V/PI double positive stained CART cells of two MM patients. CART cells with specificity for CS-1 and CD317 expanded in reverse correlation with their surface expression, which corresponded to an increased apoptosis (FIG. 6). It was concluded that CS-1 and CD317 CARTs undergo self-killing and are not suitable effectors for clinical use.

Figure 8:
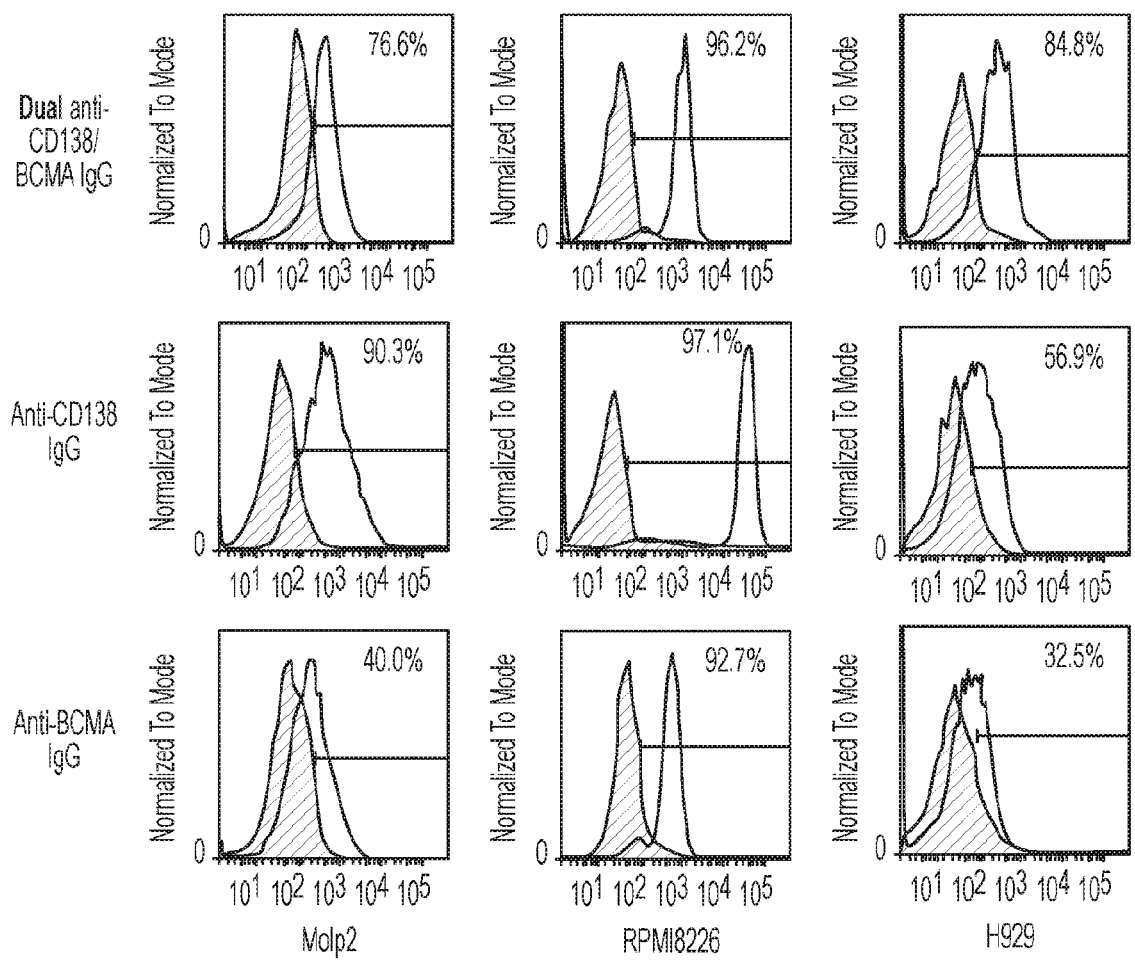
FIG. 8 is an exemplary illustration of the antigen binding function of exemplary bi-specific CD138 and BCMA scFv fusion IgG tested with three different MM cell lines.

Next a dual CAR specific for CD138 and BCMA was produced. To determine the binding affinity of the antigen-binding domain, the antigen-binding domain was fused to a Fc domain and tested with MM cell lines. The results in FIG. 8 demonstrate that the dual CD138/BCMA IgG bound both CD138 and BCMA on three different MM cell lines (Molp2, RPMI8226 and H929) with binding activities similar to either anti-CD138 Ab or anti-BCMA Ab alone. In particular, H929 expressed low levels of BCMA and CD138, but bound the dual CD138/BCMA IgG at higher efficiency (84.8% vs. 56.9% and 32.5%).

Figure 9A:
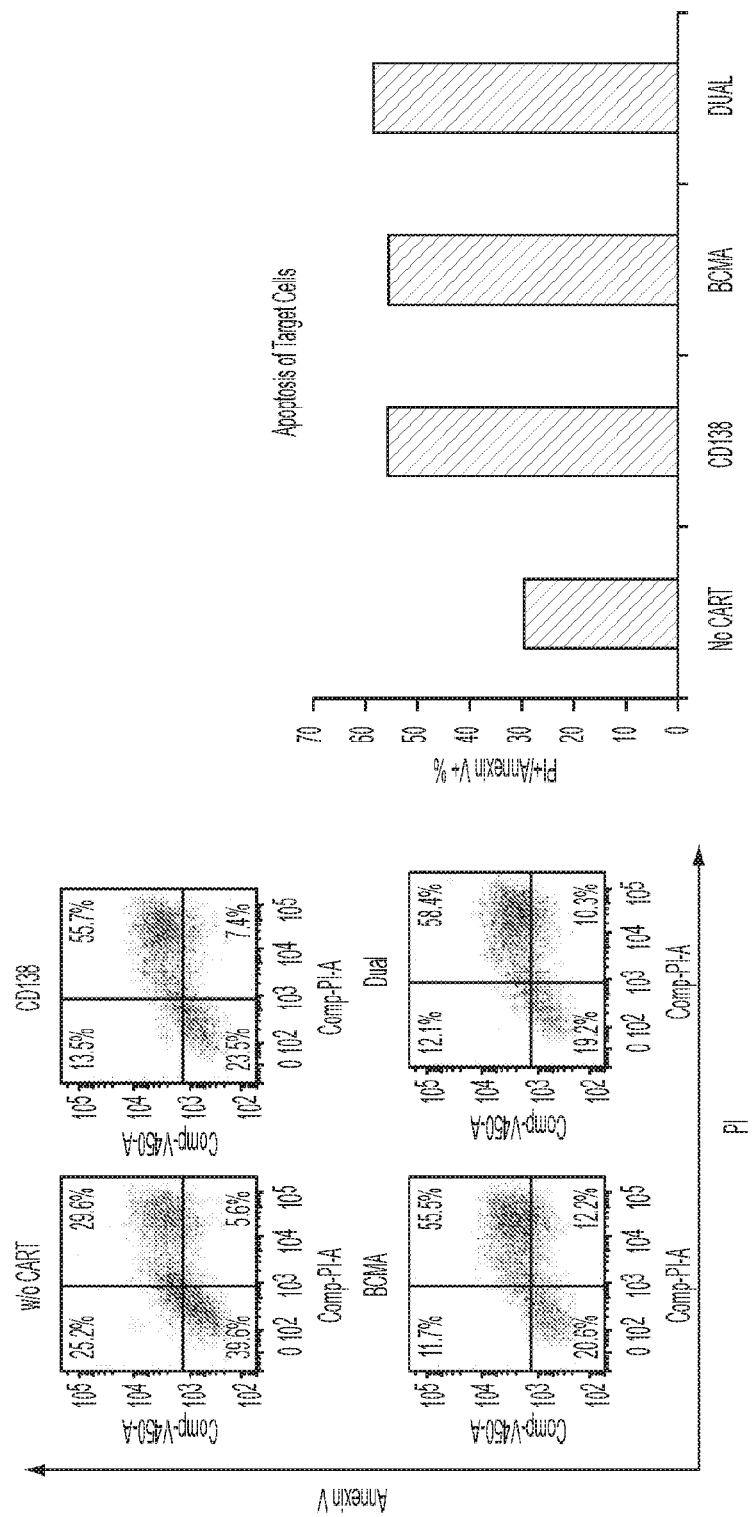
FIGS. 9A-C are a series of exemplary plots, a graph, and a photograph showing short term and repeated MM-specific killing assay of the exemplary dual CARTs.
Figure 9B:
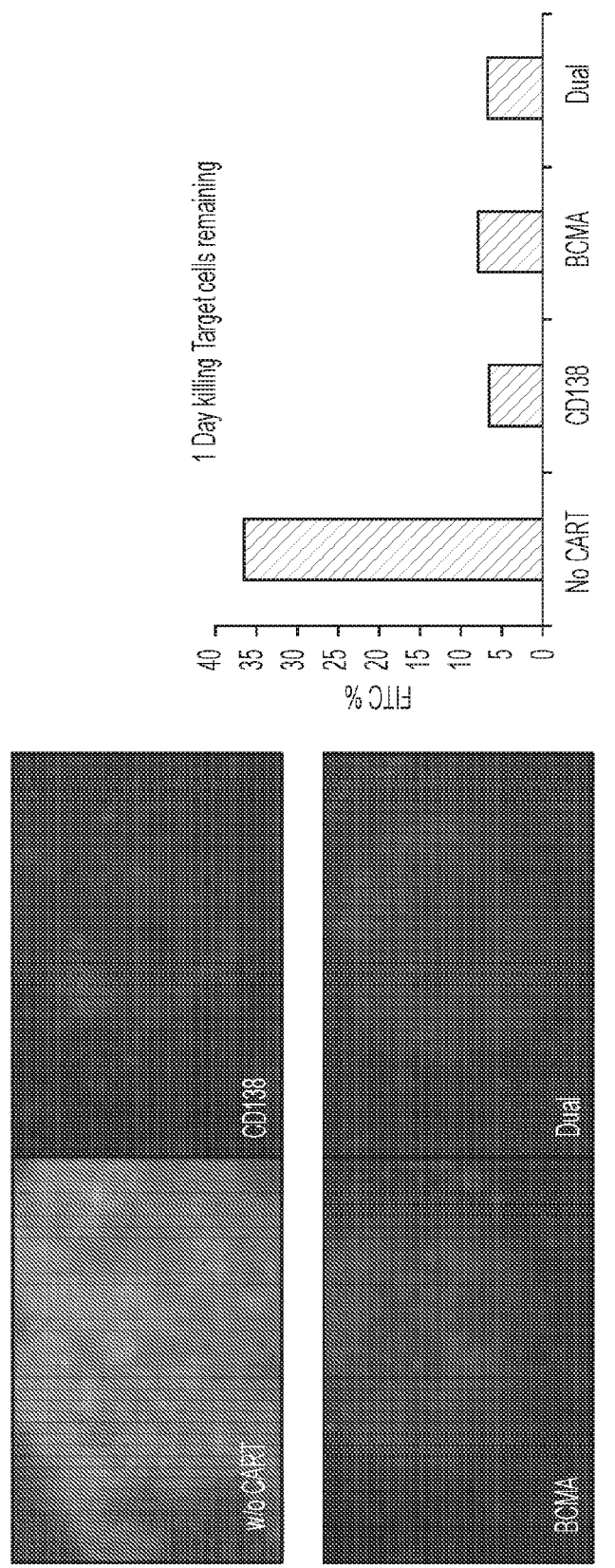
Figure 9C:
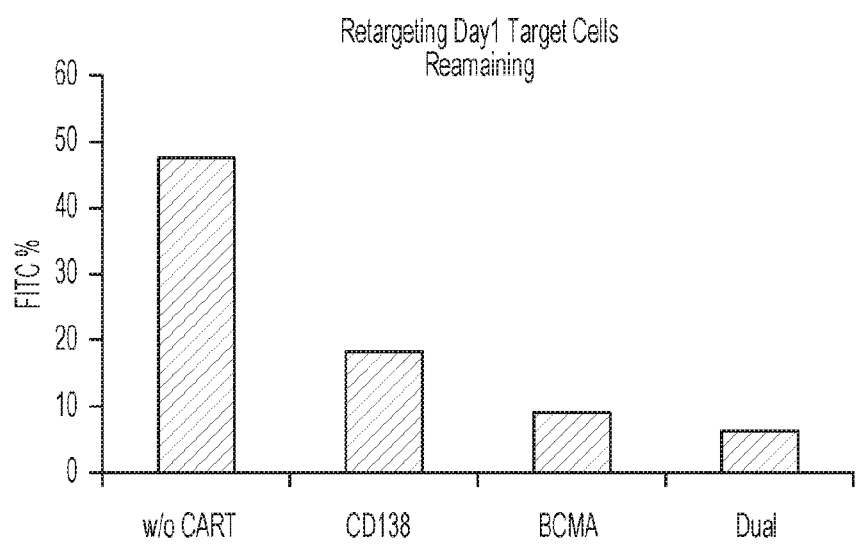
Figure 10B:
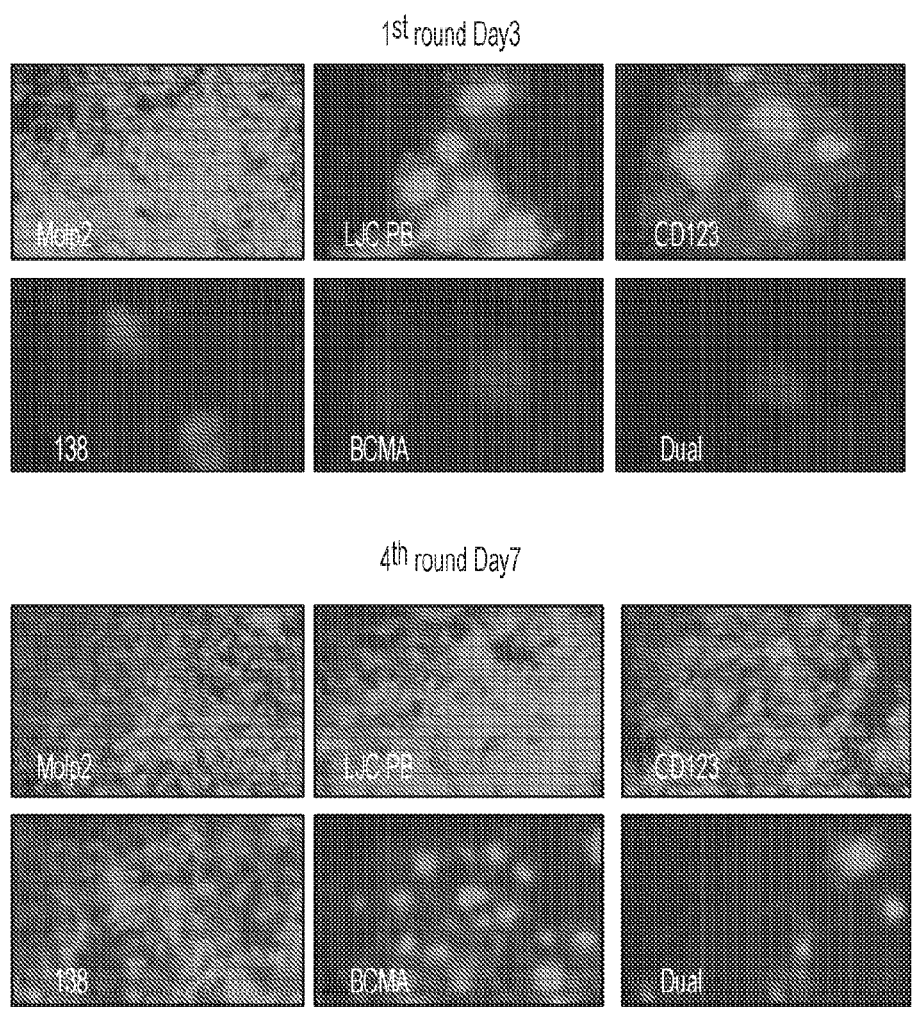
Figure 10C:
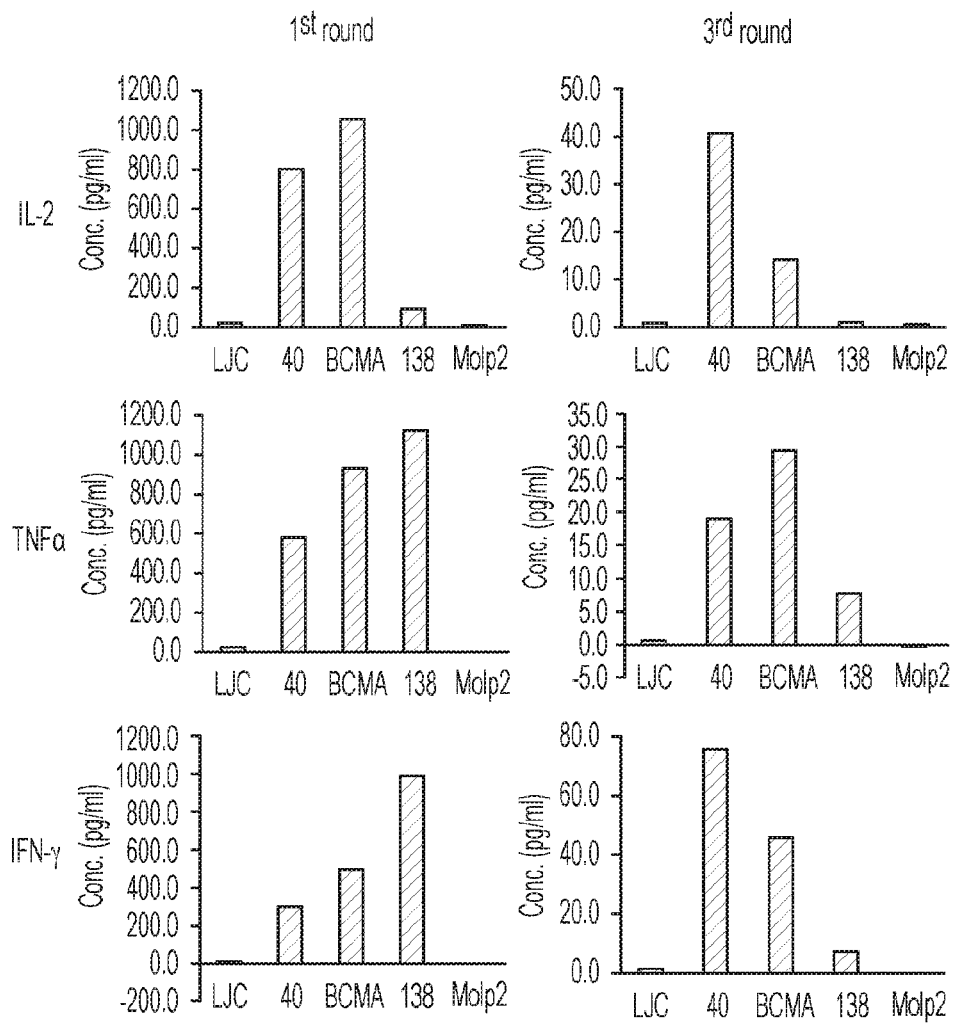
FIG. 10C are a series of plots showing effector cytokine activities of CARTs after killing MM targets. Although BCMA CARTs produced more cytokines than the dual CARTs in the 1st round killing, the dual CARTs showed prolonged function in the 3rd round killing.

FIG. 9 shows short term MM-specific killing assay of CARTs. Various CARTs were cocultured with GFP+ Molp2 MM cells for 24 hr and flow cytometry analysis shows specific target killing with CD138, BCMA and 138/BCMA dual CARTs. At 1st round killing day 3, almost all MM cells were killed by the CD138, BCMA and dual CARTs. In the 4th round killing cocultures (day 7), the dual CARTs displayed the most effective killing ability compared to all other CARTs (FIG. 10).

Figure 5:
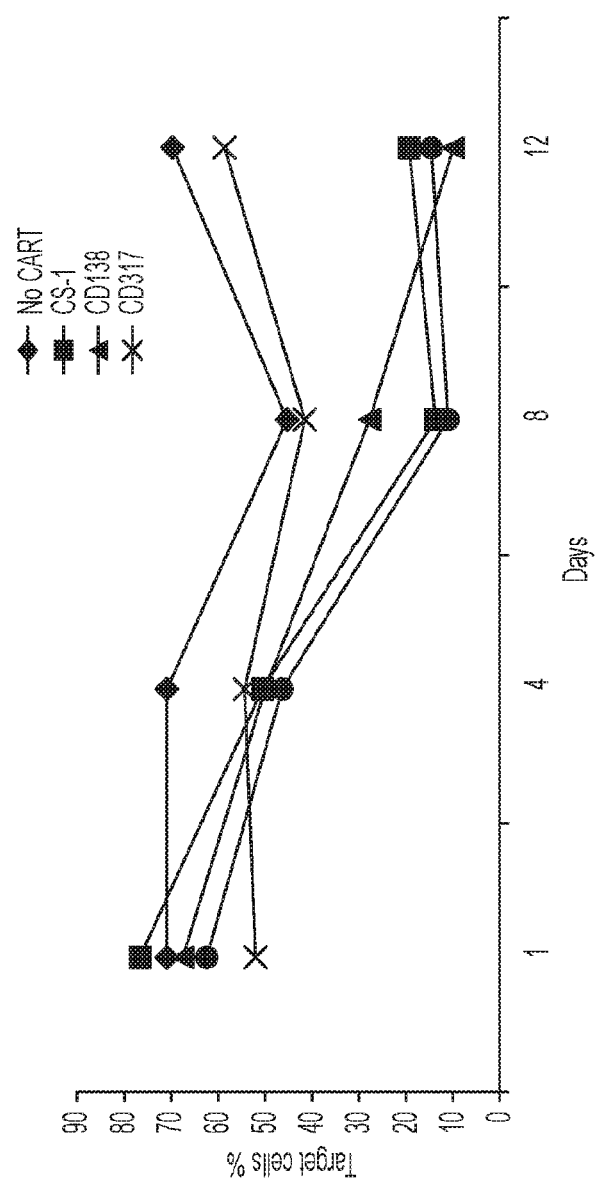
FIG. 5 is an exemplary kinetic analysis of target MM cells cocultured with different exemplary CARTs. After all target cells were killed after $1^{st}$ round coculture, the effector cells from the $1^{st}$ round coculture were supplemented with more MM target cells to set up retargeting (E/T ration=⅓).
Figure 7A:
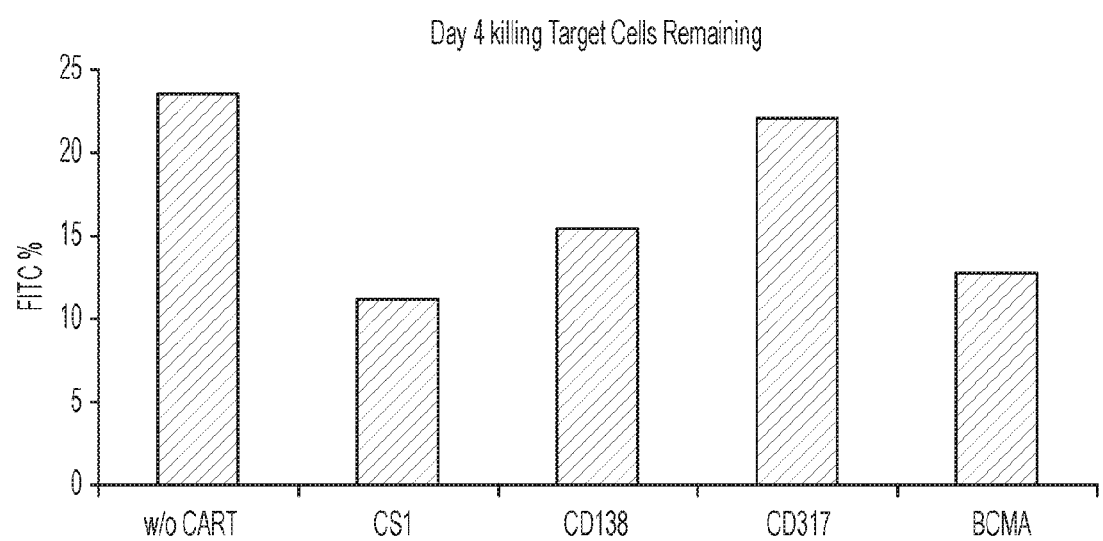
FIGS. 7A and B are a series of exemplary graphs showing primary MM patient target cell number after coculturing with CART cells of MM patients.
Figure 7B:
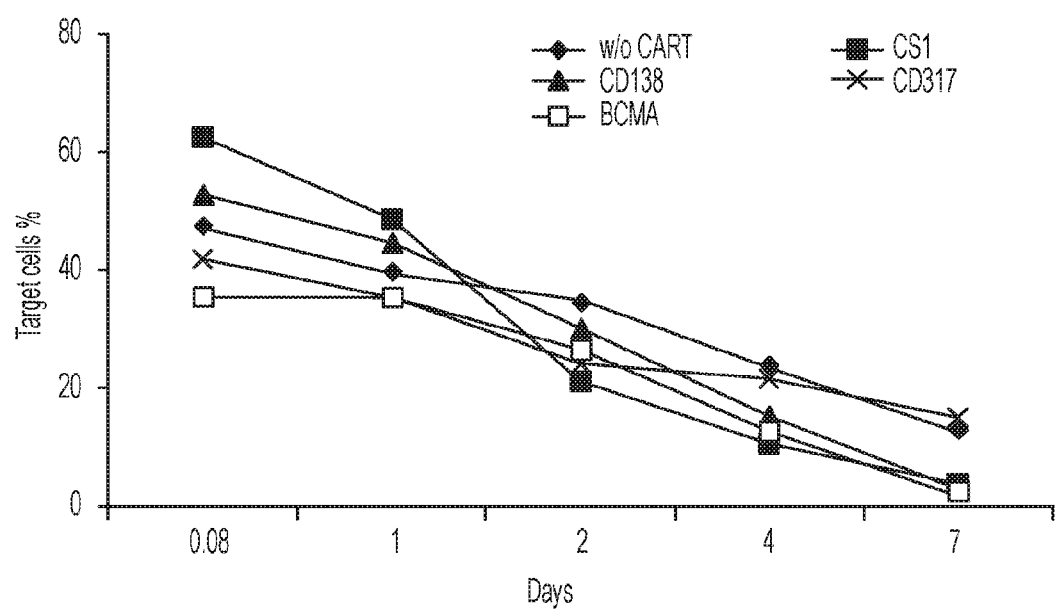
FIG. 7B shows the target cells remaining from day 0 to day 7 of coculture with exemplary CARs.

Other data showing the efficacy of the tested CARs is shown in FIGS. 5 and 7, which show killing of target cells upon co-culture with the various CARS.

This study has illustrated that multiple lenti-CAR modified T cells (CARTs) displayed highly specific and effective target-killing activities against MM. The established CART system based on four MM antigen-targeting scFvs, CD138, CD317, CS1 and BCMA, have great potential for eliminating residual disease often experienced by MM patients. Here the potential of a novel CD138/BCMA dual antigen targeting CART was illustrated, which has greater and prolonged killing ability compared to single antigen targeting CART. This powerful platform may herald the era of targeted immune cell therapy realizing the dream of a "magic bullet" for cancer treatment. Clinical trials with the MM-specific dual CD138/BCMA CARTs have been proposed.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in some embodiments, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in some embodiments, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B", the application also contemplates alternative embodiments including "a composition consisting of A and B" and "a composition consisting essentially of A and B".

What is claimed is:

1. A chimeric antigen receptor (CAR) comprising:
   (i) a first single chain Fv (scFv) specific for CD138 comprising the amino acid sequence set forth in SEQ ID NO: 36; and
   (ii) a second single chain Fv (scFv) specific for BCMA comprising the amino acid sequence set forth in SEQ ID NO: 38.

2. The CAR of claim 1, where the CAR further comprises a CD28 transmembrane domain and/or a co-stimulatory domain and/or a signaling domain.

3. The CAR of claim 2, wherein the co-stimulatory domain is a 4-1BB co-stimulatory domain and/or the signaling domain is a CD27 signaling domain.

4. The CAR of claim 1, wherein the CAR comprises a CD3zeta signal transduction domain.

5. The CAR of claim 1, wherein the CAR further comprises one or more of a CD28 transmembrane domain, a 4-1BB co-stimulatory domain, a CD27 domain, and a CD3zeta signal transduction domain.

6. The CAR of claim 1, further comprising a caspase 9 functional domain and/or a mutated FK506 binding protein (FKBP) motif.

7. The CAR of claim 1, wherein the CAR is
   (i) a homodimer; or
   (ii) a heterodimer which comprises a first polypeptide and a second polypeptide, wherein the first polypeptide comprises the scFv specific for CD138 and the second polypeptide comprises the scFv specific for BCMA.

8. The CAR of claim 7, wherein each of the first and second polypeptide further comprise, independently, one or more of a CD28 transmembrane domain, a 4-1BB co-stimulatory domain, a CD27 signaling domain and a CD3zeta signal transduction domain.

9. The CAR of claim 8, wherein each of the first and second polypeptide further comprise, independently, a caspase 9 functional domain and a mutated FK506 binding protein (FKBP) motif.

10. The CAR of claim 1, wherein the CAR further comprises a CD28 extracellular domain.

11. A nucleic acid comprising a sequence that encodes the CAR of claim 1.

12. A lentiviral vector comprising the nucleic acid of claim 11.

13. A cell comprising the CAR of claim 1.

14. The cell of claim 13, wherein the cell is a stem cell, NK cell, or T cell.

15. A composition comprising a plurality of the cell of claim 13.

16. A method of generating a plurality of CAR modified cells, the method comprising:
    introducing one or more lentiviral vectors comprising the nucleic acid of claim 11 into a plurality of immune cells.

17. The method of claim 16, wherein the immune cells are T cells.

18. A method of treating a subject having cancer or at risk of having cancer, the method comprising:
    administering the cell of claim 13 into a subject having cancer or at risk of having cancer.

19. The method of claim 18, wherein the cancer is multiple myeloma.

* * * * *